United States Patent
Han

(10) Patent No.: US 9,670,548 B2
(45) Date of Patent: Jun. 6, 2017

(54) METHODS OF DIAGNOSING COLORECTAL CANCER BY DETECTING FADA EXPRESSION

(71) Applicant: Case Western Reserve University, Cleveland, OH (US)

(72) Inventor: Yiping Han, Beachwood, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/163,395

(22) Filed: Jan. 24, 2014

(65) Prior Publication Data

US 2014/0206011 A1 Jul. 24, 2014

Related U.S. Application Data

(60) Provisional application No. 61/756,204, filed on Jan. 24, 2013, provisional application No. 61/863,231, filed on Aug. 7, 2013.

(51) Int. Cl.
C12Q 1/68 (2006.01)
C07H 21/02 (2006.01)
C07H 21/04 (2006.01)

(52) U.S. Cl.
CPC .......... *C12Q 1/6886* (2013.01); *C12Q 1/689* (2013.01); *C12Q 2600/158* (2013.01)

(58) Field of Classification Search
None
See application file for complete search history.

(56) References Cited

U.S. PATENT DOCUMENTS

| 2012/0027799 A1* | 2/2012 | Sears et al. ................ 424/246.1 |
| 2013/0259899 A1* | 10/2013 | Allen-Vercoe et al. ... 424/234.1 |
| 2014/0024036 A1* | 1/2014 | Wang et al. ................ 435/6.12 |
| 2014/0107092 A1* | 4/2014 | Meyerson et al. ............ 514/196 |

FOREIGN PATENT DOCUMENTS

WO WO 2012/045150 * 4/2012

OTHER PUBLICATIONS

Han et al. J Bacteriology. 2005. 187: 5330-5340.*
Castellarin, Mauro, et al., "Fusobacterium nucleatum infection is prevalent in human colorectal carcinoma", Genome Res. 2012 22: 299-306, Oct. 18, 2011.
Kostic, Aleksandar D, et al., "Genomic analysis identifies association of Fusobacterium nucleatum with colorectal carcinoma", Genome Res. 2012 22: 292-298, Oct. 18, 2011.

* cited by examiner

*Primary Examiner* — Carla Myers
(74) *Attorney, Agent, or Firm* — Tarolli, Sundheim, Covell & Tummino LLP

(57) ABSTRACT

A method of identifying a subject with increased risk of colorectal cancer includes obtaining a biological sample from the subject, measuring the level of *Fusobacterium nucleatum* in the biological sample, and comparing the measured level to a control level, wherein an increased measured level compared to the control level is indicative of increased risk of colorectal cancer in the subject.

9 Claims, 8 Drawing Sheets

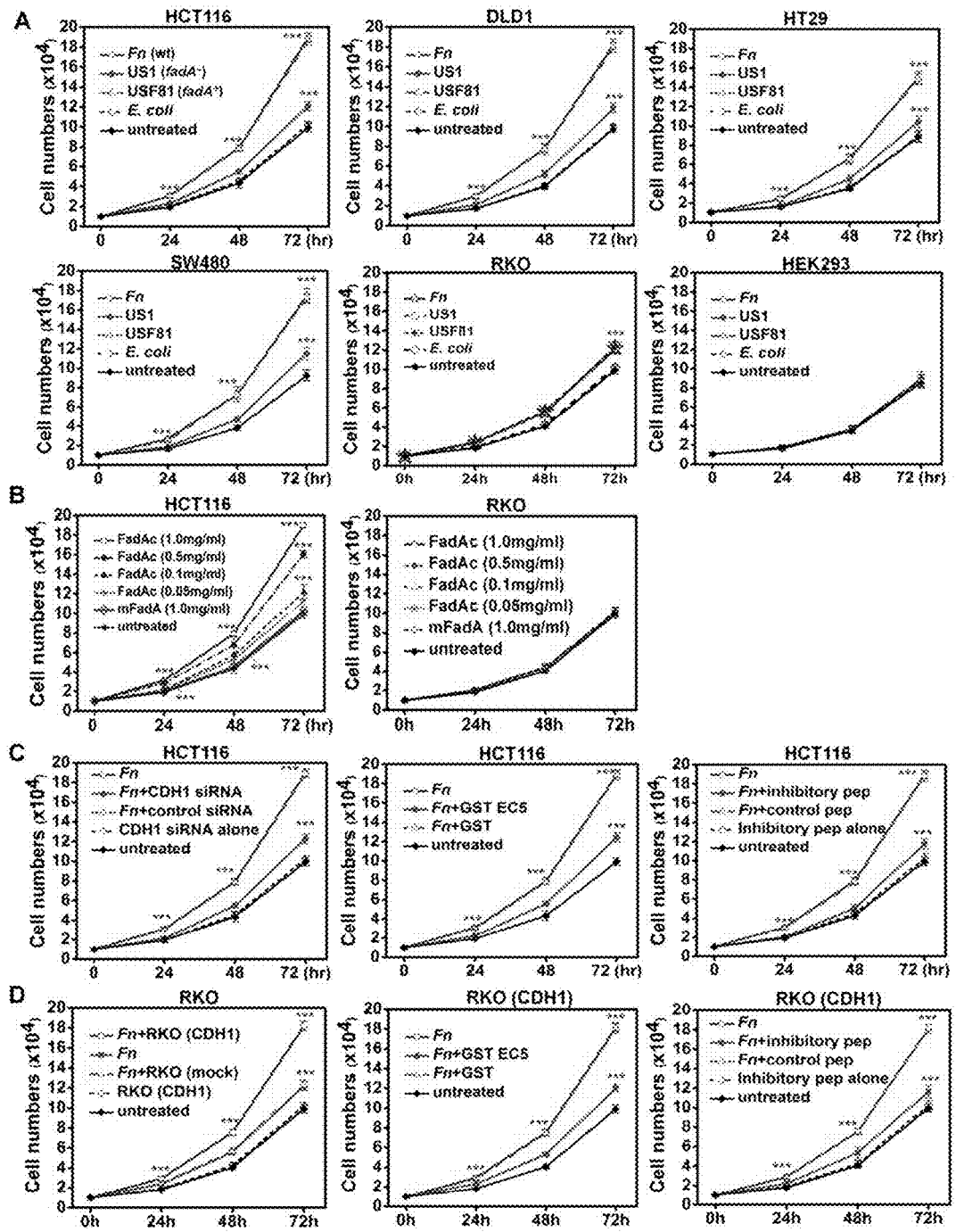
Figs. 1A-D

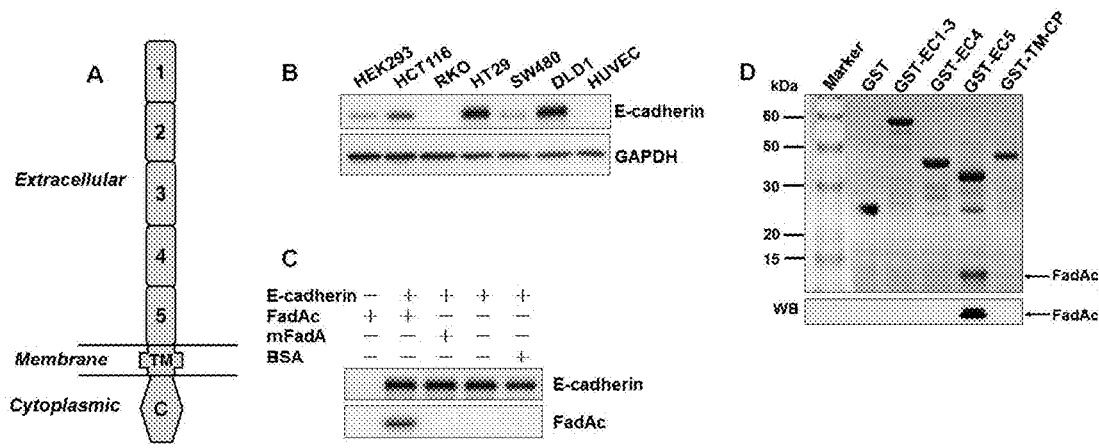
Figs. 2A-D
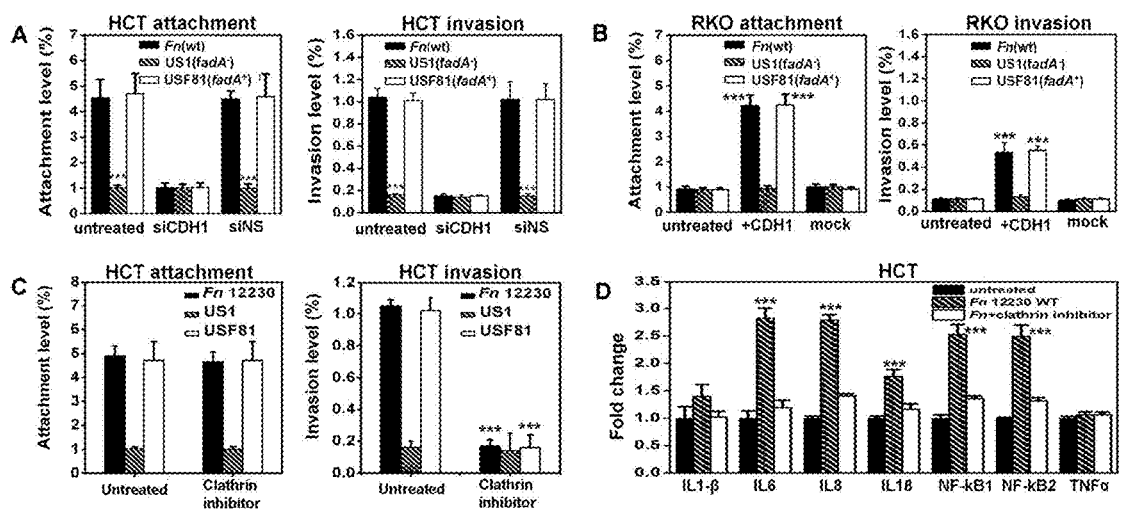
Figs. 3A-D

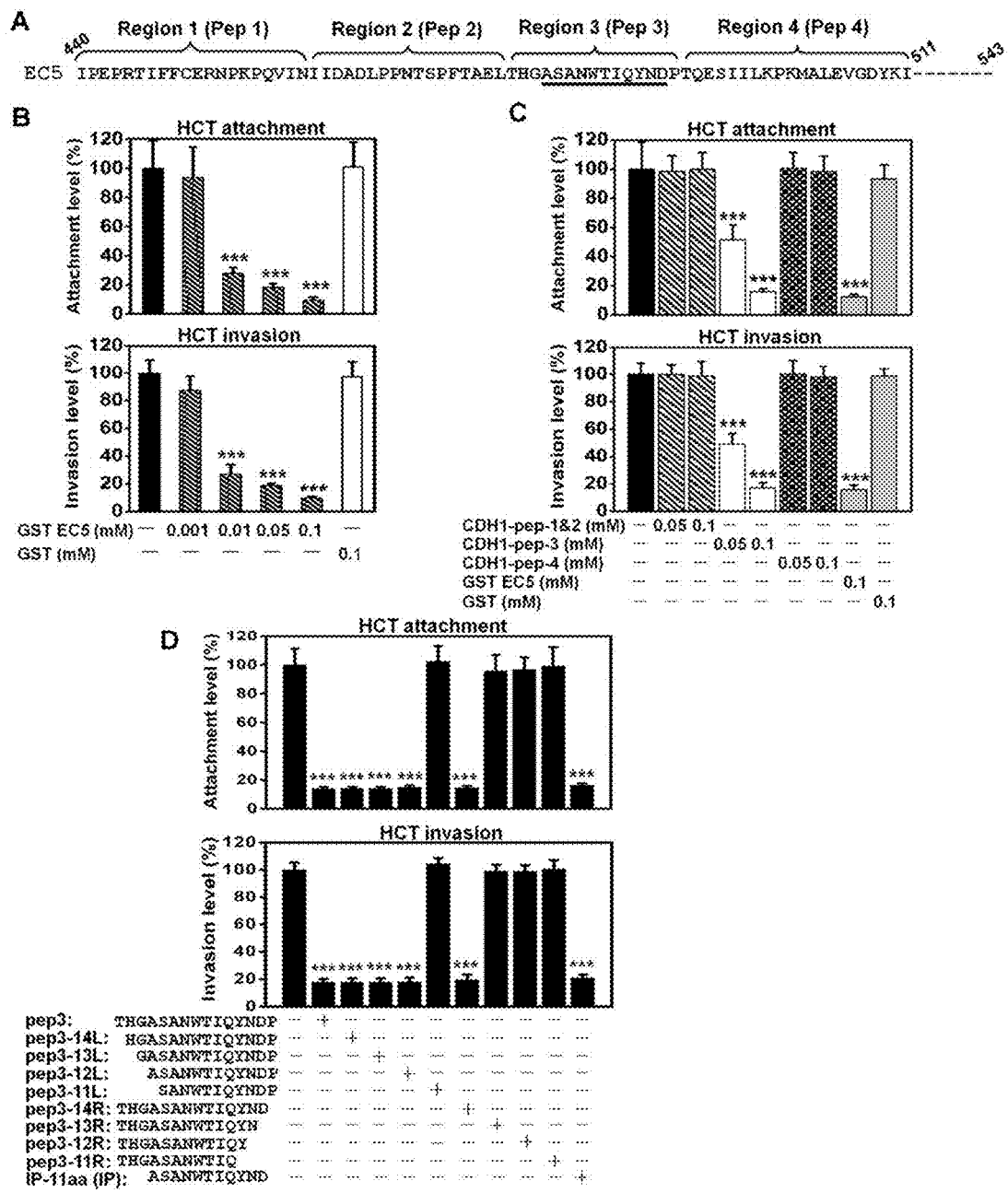
Figs. 4A-D

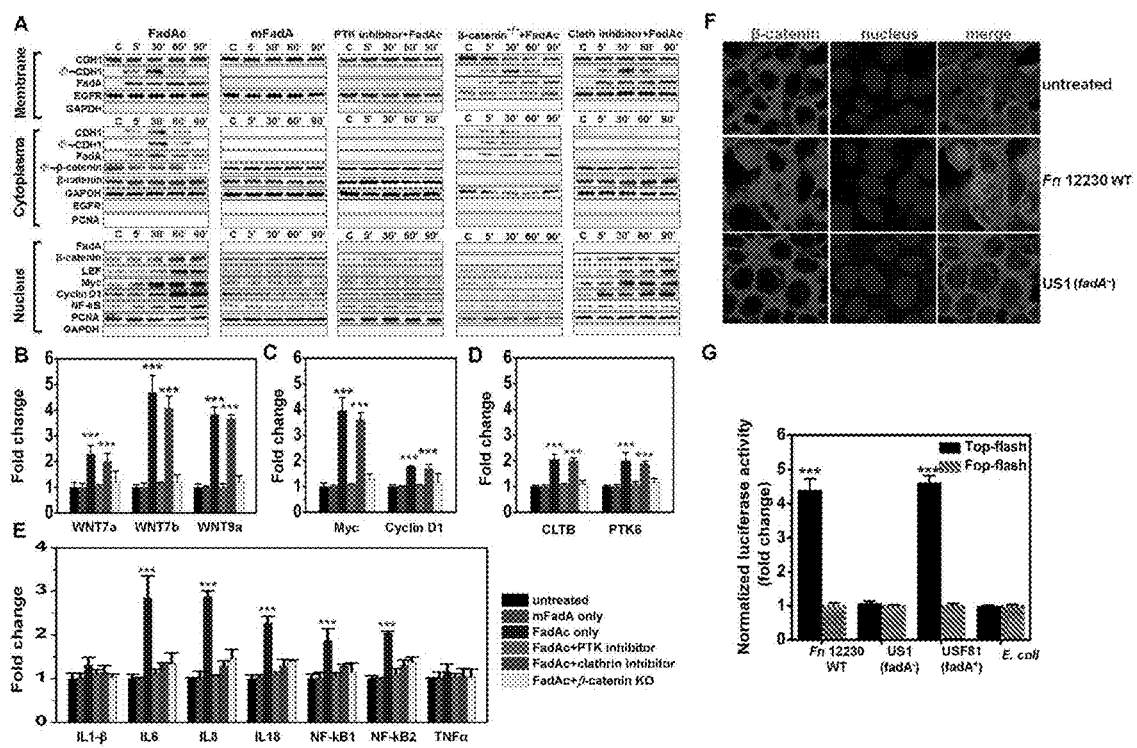
Figs. 5A-G

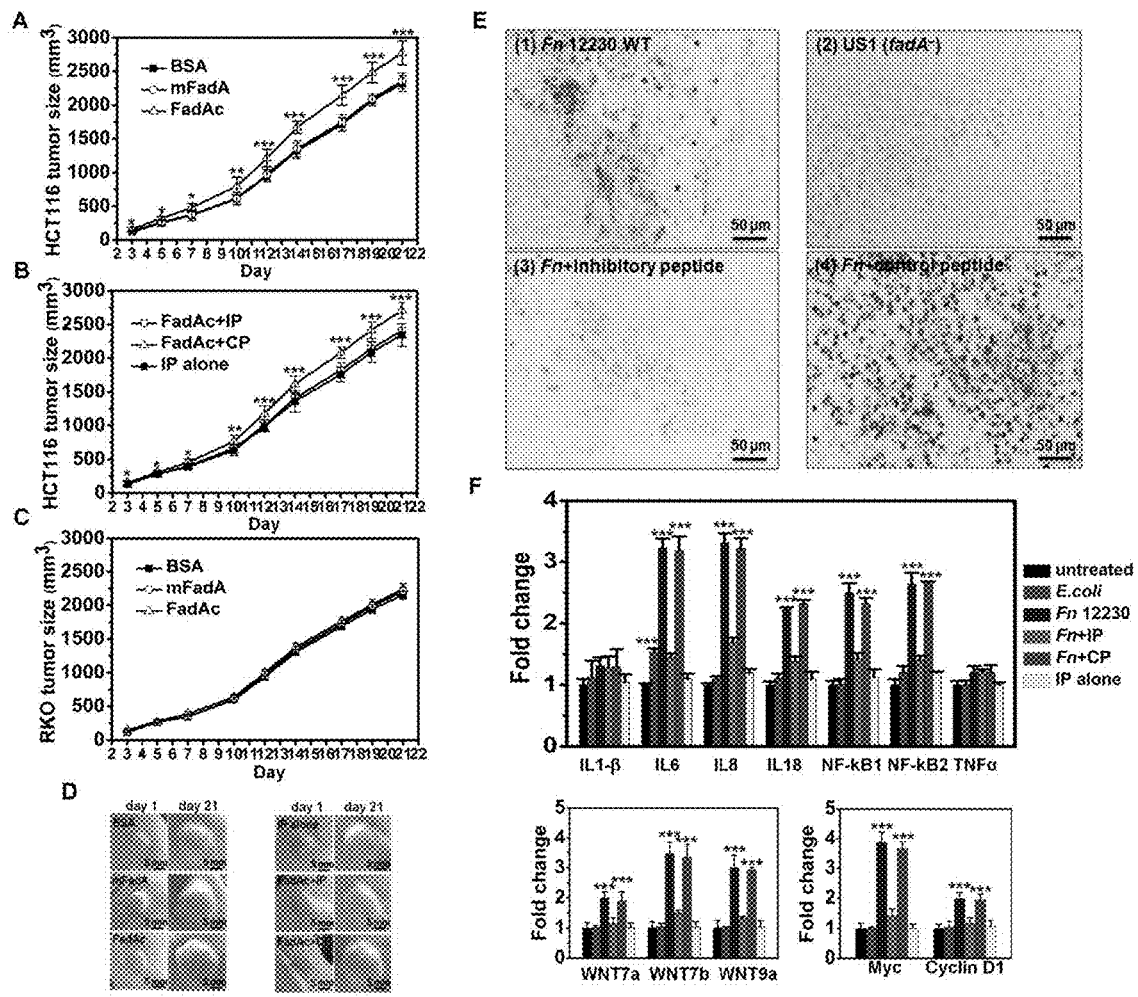
Figs. 6A-F

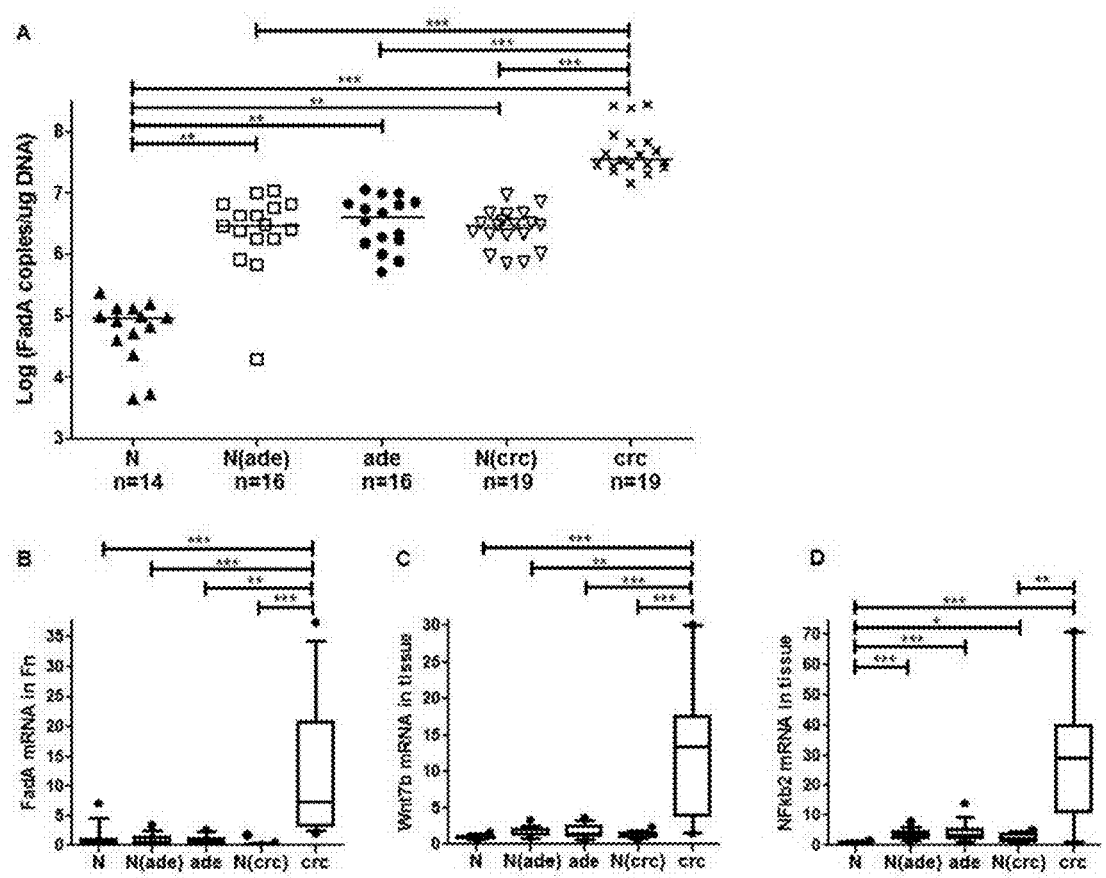
Figs. 7A-D

US 9,670,548 B2

METHODS OF DIAGNOSING COLORECTAL CANCER BY DETECTING FADA EXPRESSION

RELATED APPLICATION

This application claims priority from U.S. Provisional Application Nos. 61/756,204, filed Jan. 24, 2013 and 61/863,231 filed Aug. 7, 2013, the subject matter of which are incorporated herein by reference in their entirety.

GOVERNMENT FUNDING

This invention was made with government support under Grant No. RO1 DE014924 awarded by The National Institute of Health. The United States government has certain rights to the invention.

BACKGROUND

The human intestinal microbiome contains greater than 1000 different species totaling $10^{14}$ microorganisms and plays an important role in the maintenance of the normal physiology of the gut, including energetic metabolism, proliferation and survival of epithelial cells, and protection against pathogens. The microbiota exerts both beneficial and detrimental effects on host contributing to healthy or disease. Recently, two research teams simultaneously reported overabundance of a specific microorganism, *Fusobacterium nucleatum* (Fn), in colorectal carcinoma (CRC) tissues. However, it was unknown if Fn was a cause or a consequence of CRC.

Fn is an opportunistic commensal anaerobe in the oral cavity, implicated in various forms of periodontal diseases. Outside the oral cavity, it is one of the most prevalent species in extra-oral infections. It is highly prevalent in intrauterine infections associated with pregnancy complications such as preterm birth, stillbirth, and neonatal sepsis. Fn adheres to and invades endothelial and epithelial cells, a likely mechanism utilized for its systemic dissemination.

SUMMARY

Embodiments described herein relate to a method of identifying a subject with increased risk of colorectal cancer. The method includes obtaining a biological sample from the subject. The level of *Fusobacterium nucleatum* in (Fn) the biological sample is measured. The measured level is compared to a control level. An increased measured level compared to the control level is indicative of increased risk of colorectal cancer in the subject.

In some embodiments, the biological sample includes at least one of colon biopsies, saliva, rectal swabs, or a bodily fluid. The bodily fluid can include at least one of blood, amniotic fluid, lung aspirate, saliva, or synovial fluid.

In other embodiments, the level of *Fusobacterium nucleatum* in the sample is measured by measuring FadA expression in the sample. The FadA expression can be measured by measuring FadA mRNA levels in the sample. The FadA expression can also be measured by measuring FadA protein levels in the sample. The level of *Fusobacterium nucleatum* in the sample can also measured by measuring *Fusobacterium nucleatum* (Fn) 16S rRNA levels in the sample.

In still other embodiments, the method can include measuring Fn 16S rRNA levels and normalizing the measured Fada mRNA levels to the Fn 16S rRNA levels. An increased normalized Fada mRNA level is indicative of the subject having colorectal cancer.

Still other embodiments relate to a method of differentiating precancerous and cancer states in a subject at risk of or suspected of having colorectal cancer. The method can include obtaining a biological sample from the subject. The level of *Fusobacterium nucleatum* in the biological sample is measured. The measured level is then compared to a control level. An increased measured level compared to the control level is indicative of the subject having colorectal cancer.

Other embodiments described herein relate to a method of measuring the efficacy of a therapeutic in treating colorectal cancer in a subject. The method can include administering the therapeutic to the subject. A biological sample can be obtained from the subject after administration of the therapeutic. The level of *Fusobacterium nucleatum* in the biological sample is measured. The measured level is compared to a control level. A decreased measured level compared to the control level is indicative of increased efficacy of the therapeutic in treating colorectal cancer in the subject.

Other embodiments described herein relate to a method of inhibiting *Fusobacterium nucleatum* (Fn) colonization in a subject. The method includes administering to the subject a therapeutically effective amount of a therapeutic agent that inhibits FN binding to or complexing with cadherin in a subject.

In some embodiments, the therapeutic agent inhibits FadA binding to E-cadherin and/or VE-cadherin and the colonization of Fn can lead to an adverse outcome in the subject. In other embodiments, the cadherin is expressed by a cancer cell, such as a colorectal cancer cell.

In other embodiments, the therapeutic agent includes a small molecule or therapeutic polypeptide. The therapeutic polypeptide can consist of about 10 to about 50 amino acids and has an at least 80% sequence identity with about 10 to about 50 consecutive amino acids of E-cadherin or VE-cadherin and to which FadA binds. In some embodiments, the therapeutic polypeptide can have the amino acid sequence of ASANWTIQYN (SEQ ID NO: 1) or NNFTLTDNHDN (SEQ ID NO: 2).

Still other embodiments relate to a method of treating colorectal cancer in a subject. The method includes administering to the subject a therapeutically effective amount of a therapeutic agent that inhibits Fn binding to or complexing with colorectal cancer cells in the subject. In some embodiments, the therapeutic agent can inhibit FadA binding to E-cadherin and/or VE-cadherin that is expressed by colorectal cancer cells.

In other embodiments, the therapeutic agent includes a small molecule or therapeutic polypeptide. The therapeutic polypeptide can consist of about 10 to about 50 amino acids and has an at least 80% sequence identity with about 10 to about 50 consecutive amino acids of E-cadherin or VE-cadherin and to which FadA binds. In some embodiments, the therapeutic polypeptide can have the amino acid sequence of ASANWTIQYN (SEQ ID NO: 1) or NNFTLTDNHDN (SEQ ID NO: 2). In yet other embodiments, a clathrin inhibitor can be administered to the subject.

Still other embodiments relate to a therapeutic agent that includes a therapeutic polypeptide that consists of about 10 to about 50 amino acids and has an at least 80% sequence identity with about 10 to about 50 consecutive amino acids of E-cadherin or VE-cadherin and to which FadA binds. The therapeutic polypeptide can have the amino acid sequence of ASANWTIQYN (SEQ ID NO: 1) or NNFTLTDNHDN (SEQ ID NO: 2).

BRIEF DESCRIPTION OF THE DRAWINGS

FIG. 1 illustrates plots showing Fn and FadA stimulate proliferation of human colon cancer cells via E-cadherin. A. Wild type Fn (Fn) and the fadA-complementing USF81 (fadA+) stimulated proliferation of human CRC cells HCT116, DLD1, SW480, and HT29, compared to untreated cells or those incubated with E. coli. US1 (fadA−) only weakly stimulated their growth. Fn, USF81 and US1 all weakly stimulated the growth of CRC cells RKO, but not the non-CRC cells HEK293. B. Purified FadAc stimulated HCT116 cell growth in a dose-dependent manner, while mFadA did not. Neither FadAc nor mFadA stimulated RKO cell growth. C. Suppression of Fn-stimulated cell growth by inhibiting E-cadherin. Fn-stimulated HCT116 growth was inhibited by siRNA specific for CDH1, GST-EC5 fusion protein, and the inhibitory peptide (IP), but not by non-specific siRNA, GST, or the control peptide (CP). D. Fn stimulated the growth of RKO cells transfected with CDH1, but not mock-transfected RKO. Growth stimulation of CDH1-transfected RKO cells was suppressed by GST-EC5 and the inhibitory peptide, but not by GST or the control peptide. The results are presented as mean±SD. ***p<0.001. See also Figure S3.

FIG. 2 illustrates: A. Schematic representation of the E-cadherin (CDH1) structure. E-cadherin has five extracellular cadherin (ECs) repeats, numbered EC1-5 starting from N-terminal. TM, transmembrane domain; C, cytoplasmic domain. B. Western blot showing E-cadherin is expressed in epithelial cell HEK293 and most CRC cells. E-cadherin in HEK293 and human CRC cell lines HCT116, RKO, HT29, SW480 and DLD1. Human umbilical vein endothelial cells (HUVEC) were included as a negative control. The endogenous GAPDH was used as a loading control. C. Western blot showing E-cadherin co-immunoprecipitates with FadAc. HEK293 cell lysate expressing E-cadherin was mixed with E. coli lysates expressing FadAc, or mFadA, or BSA, followed by incubation with mouse anti-CDH1 monoclonal antibodies (mAb) and captured with agarose A/G beads. D. FadA binds to EC5. Purified GST or GST-fusion proteins carrying EC1-3, EC4, or EC5 were incubated with E. coli lysates expressing FadAc, followed by capture with GST resin. The eluted components were subjected to SDS-PAGE, followed by Coommassie blue staining (top panel) and Western blot (WB) using anti-FadA mAb 5G11-3G8 (bottom panel).

FIG. 3 illustrates graphs showing Fn adheres to and invades E-cadherin-expressing CRC cells. A. Fn adheres to and invades the E-cadherin-expressing HCT116 via FadA and E-cadherin. The fadA-deletion mutant US1 (fadA−) was defective for attachment and invasion, compared to wild type Fn and the fadA-complementing clone USF81 (fadA+). Transfection with siRNA to inhibit E-cadherin expression (siCDH1) reduced attachment and invasion, while the non-specific siRNA (siNS) did not. B. Wild-type Fn, US1, and USF81, were defective for attachment and invasion of the non-E-cadherin-expressing RKO cells. Transfection of full-length CDH1 into RKO enhanced attachment and invasion by wild type Fn and USF81 (fadA+), but not by US1 (fadA−). C. The clathrin inhibitor, Pitstop2, inhibits Fn and USF81 (fadA+) invasion of HCT116, without affecting their attachment. D. Wild type Fn stimulates expression of NF-kappaB and pro-inflammatory cytokines IL-6, 8, and 18 in HCT116, which was inhibited by the clathrin inhibitor. Expression levels in untreated HCT116 were designated as "1". For A, B, and D, the attachment and invasion levels were expressed as percent bacteria recovered from the host cells relative to the initial inoculum. For wild type Fn, these levels reflect recovering approximately 9000 CFU per well (in a 96-well plate) from the attachment assay and approximately 2000 CFU from the invasion assay. The invasion level of E. coli DH5α into HCT116 was <0.01%, i.e., <20 CFU recovered per well (data not shown). For C, the original attachment (4.4±0.8%) and invasion (1.3±0.1%) levels without inhibition were designated as "100%", and the relative inhibition values were shown. The results were presented as the mean±SD. ***p<0.001.

FIG. 4 illustrates: A. Schematic illustration of partial amino-acid sequence of the EC5 domain (SEQ ID NO: 54). The regions and the corresponding peptides (pep) are shown above the sequence. The sequences corresponding to the inhibitory peptide (IP, see below) (SEQ ID NO: 1) are underlined. Peptide 4 was the control peptide (CP) in all studies. B. Purified GST-EC5 fusion protein inhibits wild type Fn attachment and invasion of HCT116 in a dose-dependent manner. C. Fn attachment and invasion of HCT116 cells were inhibited by a synthetic peptide corresponding to region 3 (pep 3) on the EC5 domain, not by peptides corresponding to regions 1&2, or 4. D. The inhibitory effects of synthetic oligopeptides carrying sequential deletions from the N- and C-termini of region 3 on Fn attachment and invasion. (SEQ ID NOs: 55-64). Deletion of 3 residues from N-terminal and 1 residue form C-terminal did not affect the inhibitory function. An 11-aa peptide (ASANWTIQYND) (SEQ ID NO: 64) was found as the minimum sequence required for inhibition of Fn attachment and invasion. All values were expressed as relative to those without inhibition, which were designated as "100%". The actual attachment and invasion levels were 6.3±1.4% and 1.6±0.1%, respectively, for B, and 5.9±0.7% and 1.4±0.1%, respectively, for C. The results are presented as mean±SD. ***p<0.001.

FIG. 5 illustrates immunoassays and graphs showing FadAc activates E-cadherin-mediated cellular signaling. A. FadAc, but not mFadA, binds to the membranes of HCT116, accompanied by phosphorylation of E-cadherin on the membrane; internalization of E-cadherin and FadA, reduced phosphorylation of β-catenin, and accumulation of β-catenin in the cytoplasma; and translocation of β-catenin and activation of transcription factors lymphoid enhancer factor (LEF)/T-cell factor (TCF), NF kappaB, and oncogenes Myc and Cyclin D1 in the nuclei; all as detected by Western blot. Protein tyrosine kinase (PTK) inhibitor, Genistein, inhibits all FadAc-activated functions. No gene activation was detected in the HCT116 β-catenin$^{−/−}$ cells, despite binding and internalization of FadA and E-cadherin. The clathrin inhibitor, Pitstop2, prevented E-cadherin and FadA internalization and activation of NF kappaB, but did not affect nuclei translocation of β-catenin or expression of LEF/TCF, Myc or Cyclin D1. The epidermal growth factor receptor (EGFR), glyceraldehyde 3-phosphate dehydrogenase (GAPDH), and proliferating cell nuclear antigen (PCNA) were used as loading controls for membrane, cytoplasmic, and nucleus, respectively, and for examination for cross-contamination between the subcellular fractions. B-E. FadAc, but not mFadA or BSA, activates expression of Wnt signaling genes 7a, 7b, 9a (B), oncogenes Myc and Cyclin D1 (C), clathrin (cltb) and protein tyrosine kinase genes (ptk6) (D), and NF-kappaB and pro-inflammatory cytokines IL-6, 8, and 18 (E) in wild-type or β-catenin knockout HCT116 cells following 2 hrs incubation as determined by qPCR. The clathrin inhibitor inhibited expression of the inflammatory genes but not the Wnt or oncogenes, while inhibition of β-catenin by siRNA suppressed expression of all genes. Expression levels in untreated HCT116 were designated as "1". F. Wild type Fn (Fn), but not US1 (fadA−), induces nuclei translocation of β-catenin following 2 hrs incubation as observed by confocal microscopy. β-catenin was stained with Alex 634 and the nuclei with 4',6-diamidino-2-phenylindole (DAPI) (blue). G. Luciferase reporter gene expression following HCT116 transfection with TOPFlash (activated by (β-catenin) or FOPFlash (insensitive to β-catenin activation). Fn was incubated with the transfected cells at a MOI of 1,000:1 for 2 hours, followed by measurement of the luciferase activity. Values obtained with FOPFlash were designated as "1" and those obtained with TOPFlash were expressed as fold changes. Data are presented as mean fold changes ±SD of two independent experiments, each in triplicate. ***$p<0.001$.

FIG. 6 illustrates plots, images, and graphs showing FadA promotes E-cadherin-mediated CRC tumor growth and induction of pro-inflammatory cytokines in xenograft mice. HCT116 or RKO were injected subcutaneously and bilaterally into female nude mice, which were then randomized (5 per group) to receive treatments. A-C. FadA stimulates HCT116 but not RKO xenograft growth. Purified FadAc, mFadA, or BSA were injected into xenografts of HCT116 either alone (A), or along with the inhibitory (IP) or control (CP) peptides (B), or RKO alone (C) in nude mice. IP alone is injected into HCT116 as a negative control (B). D. Representative tumors from a and b are shown. The first day of protein injection was designated as "day 1". All tumors look the same on day 1. Notice the size increase of the tumor treated with FadAc and FadAc+CP on day 21, compared to other tumors on the same day. E. Immunohistochemical staining of xenografts infected with wild-type Fn (Fn), alone and with the inhibitory or control peptides, and the fadA-deletion mutant US1 (fadA−) using rabbit anti-Fn polyclonal antibodies. For controls, xenografts infected with wild-type Fn was stained with pre-serum, and xenografts infected with E. coli DH5α were stained with anti-Fn antibodies (data not shown). F. Wild-type Fn induces expression of NF-kappaB and pro-inflammatory cytokines IL-6, 8, and 18; Wnt 7a, 7b, and 9a; and Myc and Cyclin D1 in HCT116 xenografts, as determined by qPCR. The inductions were inhibited by IP, but not by CP. E. coli only weakly induced IL-6. The results are presented as mean±SD. ***$p<0.001$.

FIG. 7 illustrates plots showing the quantification of fadA gene copies and FadA, Wnt7b and NFkB2 expression in health, precancerous adenomas, and carcinomas. DNA and RNA were extracted from full-thickness colon specimens from the following 5 groups: (1) normal non-cancerous controls (N; n=14); (2) Normal tissues from patients with precancerous adenomas [N(ade); n=16]; (3) Precancerous adenomas (ade; n=16); (4) Normal tissues from patients with carcinomas [N(crc); n=19]; and (5) Carcinomas (crc; n=19). Gene copy numbers of fadA (A) were measured using DNA and determined using the standard curves. FadA mRNA levels in Fn were normalized to Fn 16 rRNA (B), and Wnt7b (C) and NFkb2 (D) mRNA levels were each normalized to the endogenous GAPDH. The average value of Group 1 (N) was designated "1", and the fold changes of the other groups were determined by comparing to Group 1. The horizontal bars in a represent the median values. For B-D, the boxes show the 25/75 percentiles and the lines within the boxes the median values. Whiskers show the 10/90 percentiles. *$p<0.05$, $p<0.01$ and * $p<0.001$.

DETAILED DESCRIPTION

Figure 8A:
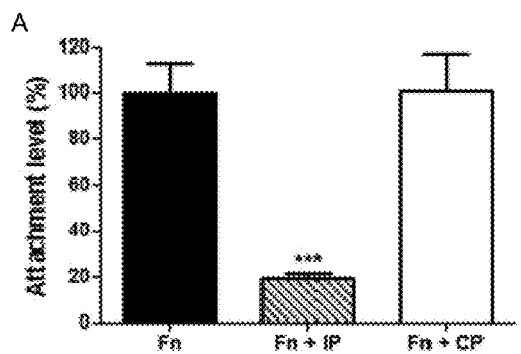
FIG. 8 illustrates inhibition of Fn attachment (A) and invasion (B) of endothelial cells. IP, inhibitory peptide; CP, control peptide.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The term "biological sample" is used herein in its broadest sense. A biological sample may be obtained from a subject (e.g., a human) or from components (e.g., tissues) of a subject. The sample may be of any biological tissue or fluid with which biomarkers of the present invention may be assayed. Frequently, the sample will be a "clinical sample", i.e., a sample derived from a patient. Such samples include, but are not limited to, bodily fluids, e.g., urine, blood, blood plasma, saliva; tissue or fine needle biopsy samples; and archival samples with known diagnosis, treatment and/or outcome history. The term biological sample also encompasses any material derived by processing the biological sample. Derived materials include, but are not limited to, cells (or their progeny) isolated from the sample, proteins or nucleic acid molecules extracted from the sample. Processing of the biological sample may involve one or more of, filtration, distillation, extraction, concentration, inactivation of interfering components, addition of reagents, and the like. In certain embodiments, a biological sample includes a colon or rectal tissue sample.

The terms "complementary" and "substantially complementary" refer to the hybridization, base pairing, or duplex formation between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. For example, selective hybridization may occur when there is at least about 65% complementary over a stretch of at least 14 to 25 nucleotides, preferably at least about 75%, and more preferably at least about 90% complementary.

The term "amplify" is used herein in the broad sense to mean creating/generating an amplification product. "Amplification", as used herein, generally refers to the process of producing multiple copies of a desired sequence, particularly those of a sample. A "copy" does not necessarily mean perfect sequence complementarity or identity to the template sequence.

The term "hybridizing" refers to the binding of two single stranded nucleic acids via complementary base pairing. The term "specific hybridization" refers to a process in which a nucleic acid molecule preferentially binds, duplexes, or hybridizes to a particular nucleic acid sequence under stringent conditions (e.g., in the presence of competitor nucleic acids with a lower degree of complementarity to the hybridizing strand). In certain embodiments of the present invention, these terms more specifically refer to a process in which a nucleic acid fragment (or segment) from a test sample preferentially binds to a particular probe and to a lesser extent or not at all, to other probes, for example, when these probes are immobilized on an array.

The terms "array", "micro-array", and "biochip" are used herein interchangeably. They refer to an arrangement, on a substrate surface, of hybridizable array elements, preferably, multiple nucleic acid molecules of known sequences. Each nucleic acid molecule is immobilized to a discrete spot (i.e., a defined location or assigned position) on the substrate surface. The term "micro-array" more specifically refers to an array that is miniaturized so as to require microscopic examination for visual evaluation.

The term "hybridization probe" or "nucleic acid probe" refers to a nucleic acid molecule to which nucleic acid molecule from a test sample can hybridize. The nucleic acid molecule from the test sample can be a short DNA sequence (i.e., an oligonucleotide), a PCR product, or mRNA isolate. Probes specifically bind to nucleic acids of complementary or substantially complementary sequence through one or more types of chemical bonds, usually through hydrogen bond formation.

The terms "labeled", "labeled with a detectable agent" and "labeled with a detectable moiety" are used herein interchangeably. These terms are used to specify that an entity (e.g., a probe) can be visualized, for example, following binding to another entity (e.g., a polynucleotide or polypeptide). The detectable agent or moiety can be selected such that it generates a signal, which can be measured and whose intensity is related to the amount of bound entity. In array-based methods, the detectable agent or moiety is also preferably selected such that it generates a localized signal, thereby allowing spatial resolution of the signal from each spot on the array. Methods for labeling polypeptides or polynucleotides are well-known in the art. Labeled polypeptides or polynucleotides can be prepared by incorporation of or conjugation to a label, that is directly or indirectly detectable by spectroscopic, photochemical, biochemical, immunochemical, electrical, optical, or chemical means. Suitable detectable agents include, but are not limited to, various ligands, radionuclides, fluorescent dyes, chemiluminescent agents, microparticles, enzymes, calorimetric labels, magnetic labels, and haptens. Detectable moieties can also be biological molecules such as molecular beacons and aptamer beacons.

The term "PCR" refers to a reaction for the in vitro amplification of specific nucleotide sequences (e.g., DNA or RNA sequences) by the simultaneous primer extension of complementary strands of the nucleotide sequences. In other words, PCR is a reaction for making multiple copies or replicates of a target nucleotide sequence flanked by primer binding sites. PCR typically comprises one or more repetitions of the following steps: (i) denaturing a target nucleotide sequence; (ii) annealing primers to primer binding sites; and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art. For example, in a conventional PCR using Taq DNA polymerase, a double-stranded target nucleotide sequence may be denatured at a temperature>90° C., primers annealed at a temperature in the range 50-75° C., and primers extended at a temperature in the range 72-78° C. Reaction volumes range from a few hundred nanoliters, e.g., 200 nl, to a few hundred μl, e.g., 200 μl. The term "PCR" encompasses derivative forms of the reaction, including but not limited to, RT-PCR, real-time PCR, nested PCR, quantitative PCR, multiplexed PCR, and the like.

The term "reverse transcription PCR," or "RT-PCR," refers to a PCR that is preceded by a reverse transcription reaction that converts a target RNA to a complementary single stranded DNA, which is then amplified.

The term "real-time PCR" refers to a PCR for which the amount of reaction product is monitored as the reaction proceeds. There are many forms of real-time PCR that differ mainly in the detection chemistries used for monitoring the reaction product.

The term "nested PCR" refers to a two-stage PCR wherein the amplified product of a first PCR becomes the sample for a second PCR using a new set of primers, at least one of which binds to an interior location of the first reaction product. "Outer primers" in reference to a nested amplification reaction refer to the primers used to generate a first reaction product, and "inner primers" refer to the one or more primers used to generate a second, or nested, reaction product.

The term "multiplexed PCR" refers to a PCR wherein multiple target sequences (or a single target sequence and one or more reference sequences) are simultaneously carried out in the same reaction mixture. Usually, distinct sets of primers are employed for each sequence being amplified.

The term "quantitative PCR" refers to a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates.

The term "primer" refers to an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

The term "target nucleotide sequence" refers to a region of a nucleotide which is to be amplified, detected, or otherwise analyzed. An oligonucleotide primer hybridizes to a region of the polynucleotide template immediately flanking the target nucleotide sequence.

The terms "antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a polypeptide to a specific binding partner when an excess of antibody reduces the quantity of the polypeptide bound to the specific binding partner by at least about 20%, 40%, 60% or 80%, and more usually greater than about 85% (as measured in an in vitro competitive binding assay).

The term "monoclonal" refers to an antibody that specifically binds to a sequence of amino acid and/or a specific epitope of an antigen.

The term "polyclonal" refers to a combination of antibodies that recognize multiple epitope sites on a single antigen.

The term "epitope" includes any protein determinant capable of specific binding to an immunoglobulin. Epitope determinants usually consist of chemically active surface groupings of molecules such as amino acids or sugar side chains and usually have specific three-dimensional structural characteristics, as well as specific charge characteristics.

The term "agent" is used herein to denote a chemical compound, a mixture of chemical compounds, a biological macromolecule, or an extract made from biological materials.

The terms "patient", "subject", "mammalian host," and the like are used interchangeably herein, and refer to mammals, including human and veterinary subjects.

The terms "peptide(s)", "protein(s)" and "polypeptide(s)" are used interchangeably herein. "Polypeptide" refers to any peptide or protein comprising two or more amino acids joined to each other by peptide bonds or modified peptide bonds (i.e., peptide isomers). "Polypeptide(s)" refers to both short chains, commonly referred as peptides, oligopeptides or oligomers, and to longer chains generally referred to as proteins.

The terms "polynucleotide sequence" and "nucleotide sequence" are also used interchangeably herein.

The term "recombinant," refers to a protein is derived from a prokaryotic or eukaryotic expression system.

The term "wild type" refers to the naturally occurring polynucleotide sequence encoding a protein, or a portion thereof, or protein sequence, or portion thereof, respectively, as it normally exists in vivo.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

The term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "gene" or "recombinant gene" refers to a nucleic acid comprising an open reading frame encoding a polypeptide, including both exon and (optionally) intron sequences.

The terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The terms "chimeric protein" or "fusion protein" refer to a fusion of a first amino acid sequence encoding a polypeptide with a second amino acid sequence defining a domain (e.g., polypeptide portion) foreign to and not substantially homologous with any domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

The term "isolated" as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

The phrases "parenteral administration" and "administered parenterally" refer to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, agent or other material other than directly into a specific tissue, organ, or region of the subject being treated, such that it enters the animal's system and, thus, is subject to metabolism and other like processes, for example, subcutaneous administration.

Embodiments described herein relate to methods of identifying a subject with increased risk of colorectal cancer by measuring the level of *Fusobacterium nucleatum* and/or FadA expression in a biological sample from the subject. It was found that FadA of *Fusobacterium nucleatum* (Fn) binds to E-cadherin on colorectal cancer cells (CRC) and non-CRC cells, mediating Fn attachment of and invasion into the cells. FadA modulates E-cadherin and activates β-catenin signaling, leading to increased expression of transcription factors, oncogenes, Wnt genes, and inflammatory genes, as well as growth stimulation of CRC cells. It was found that in colon tissue specimens obtained from normal patients (i.e., patients without adenomas or adenocarcinomas), patients with adenomas, and patients with adenocarcinomas, there is a step-wise increase of FadA gene copies from the baseline of normal patients to adenomas and normal tissues adjacent to adenomas and adenocarcinomas, and to adenocarcinomas. The "normal" tissues from patients with adenomas and adenocarcinomas are thus "pseudo-normal", compared to the non-cancerous controls. Given the fact that FadA mediates Fn binding to both CRC and non CRC cells, and the fact that the normal tissues also express E-cadherin, it is not surprising that Fn can colonize both tumor and non-tumor sites. Elevated Fn colonization in the normal tissues can predispose the host to the development of adenomas and/or adenocarcinoma, with carcinogenesis being accelerated when a mutation occurs.

The finding of elevated FadA levels in the precancerous state and the fact that FadA is unique to Fn, demonstrates that FadA expression can be used as a diagnostic marker to identify individuals at risk for developing adenomas and/or adenocarcinomas. As demonstrated in the Example below, FadA gene copy levels in biological samples obtained from a subject can be used to define healthy, precancerous, and cancerous states in the subject.

In some embodiments, a method of identifying a subject with increased risk of colorectal cancer can include obtaining a biological sample from the subject. The level of Fn in the biological sample is then measured. The measured level is compared to a control level. An increased measured level compared to the control level is indicative of increased risk of colorectal cancer in the subject.

The methods described herein may be applied to the study of any type of biological samples in which Fn levels can be measured. In some embodiments, the biological sample can include at least one of colon biopsies, saliva, rectal swabs, or a bodily fluid. The bodily fluid can also include at least one of blood, amniotic fluid, lung aspirate, saliva, or synovial fluid.

The biological sample may be obtained or collected by any manner known to those skilled in the art. When a biological sample originating from a patient with suspected as having CRC is a blood sample, this sample is obtained from a patient by taking blood by conventional methods.

When a biological sample originating from a patient is a colorectal tissue sample, the tissue sample can taken by biopsy during colonoscopy or by excision in the operating theatre or any other suitable method of intratumoral sampling.

In some embodiments, the level of Fn in the sample is measured by measuring Fada expression and/or measuring the levels of Fn 16S rRNA in the sample. The Fada expression can be measured by measuring Fada mRNA levels in the sample. For example, RNA may be extracted from the sample before analysis. Methods of RNA extraction are well known in the art (see, for example, J. Sambrook et al., "Molecular Cloning: A Laboratory Manual", 1989, 2nd Ed., Cold Spring Harbor Laboratory Press: Cold Spring Harbor, N.Y.). Most methods of RNA isolation from bodily fluids or tissues are based on the disruption of the tissue in the presence of protein denaturants to quickly and effectively inactivate RNAses. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

In certain aspects, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2nd Ed., Cold Spring Harbour Laboratory Press: New York; "Short Protocols in Molecular Biology", F. M. Ausubel (Ed.), 2002, 5th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each probe being monitored, or using thermostable DNA polymerases (such as avian myeloblastosis virus reverse transcriptase or Moloney murine leukemia virus reverse transcriptase).

In other embodiments, determination of expression levels of Fada gene copy or Fn 16S rRNA expression levels may be performed by polymerase chain reaction (PCR) (see, for example, U.S. Pat. Nos. 4,683,195; 4,683,202, and 6,040,166; "PCR Protocols: A Guide to Methods and Applications", Innis et al. (Eds.), 1990, Academic Press: New York), reverse transcriptase PCR(RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320308), one-sided PCR (Ohara et al., Proc. Natl. Acad. Sci., 1989, 86: 5673-5677), in situ hybridization (FISH or SISH), Taqman based assays (Holland et al., Proc. Natl. Acad. Sci., 1991, 88:7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan, and the like.

Nucleic acid probes for use in the detection of polynucleotide sequences in biological samples may be constructed using conventional methods known in the art. Suitable probes may be based on nucleic acid sequences encoding at least 5 sequential amino acids from regions of nucleic acids encoding a protein marker, and preferably comprise about 15 to about 50 nucleotides. A nucleic acid probe may be labeled with a detectable moiety. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well-known in the art (for a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35:135-153).

Nucleic acid probes may be used in hybridization techniques to detect polynucleotides encoding the FadA and/or Fn 16S rRNA. The technique generally involves contacting an incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of nucleic acid molecules comprising polynucleotide sequences coding FadA may involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least 60%, preferably at least 75% and more preferably at least 90% identity to a portion of nucleic acids encoding a protein marker.

Hybridization and amplification techniques described herein may be used to assay qualitative and quantitative aspects of expression of nucleic acid molecules comprising polynucleotide sequences coding for FadA and/or Fn 16S rRNA.

Alternatively, oligonucleotides or longer fragments derived from nucleic acids encoding FadA and/or Fn 16S rRNA may be used as targets in a microarray. A number of different array configurations and methods of their production are known to those skilled in the art (see, for example, U.S. Pat. Nos. 5,445,934; 5,532,128; 5,556,752; 5,242,974; 5,384, 261; 5,405,783; 5,412,087; 5,424,186; 5,429,807; 5,436,327; 5,472,672; 5,527,681; 5,529,756; 5,545,531; 5,554, 501; 5,561,071; 5,571,639; 5,593,839; 5,599,695; 5,624,711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., *Science,* 1995, 270: 467-470; M. Schena et al., *Proc. Natl. Acad. Sci. USA* 1996, 93: 10614-10619; Chen et al., *Genomics,* 1998, 51: 313324; U.S. Pat. Nos. 5,143,854; 5,445,934; 5,807,522; 5,837, 832; 6,040,138; 6,045,996; 6,284,460; and 6,607,885).

In other embodiments, the level of Fn in the sample can be measured by measuring the level of Fada protein expression levels in the sample. In general, FadA protein expression levels are determined by contacting a biological sample, such as blood or colorectal tissue samples, isolated from a subject with binding agents for FadA, determining, in the sample, the level of FadA that bind to the binding agents; and comparing the level of FadA in the sample with the level of FadA in a control sample. The binding agent can include any an entity, such as a polypeptide or antibody that specifically or selectively binds to FadA, and can be used to measure FadA levels. An entity can specifically bind or selectively bind to a polypeptide if it reacts/interacts at a detectable level with the polypeptide but does not react/interact detectably with peptides containing unrelated sequences or sequences of different polypeptides.

In some embodiments, the binding agent can be an antibody specific for a FadA. Suitable antibodies for use in the methods described herein include monoclonal and polyclonal antibodies, immunologically active fragments (e.g., Fab or (Fab)$_2$ fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., NeuroNeuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S, Neuberger et al., Nature, 1984, 312: 604-608; S. Takeda et al., Nature, 1985, 314: 452-454). Antibodies to be used in the methods of the invention can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof is bound. The bound antibodies can then be eluted from the column using a buffer with a high salt concentration.

Instead of being prepared, antibodies to be used in the methods described herein may be obtained from scientific or commercial sources.

In certain embodiments, the antibodies to FadA or anti-FadA antibodies may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinylether-maleic acid copolymer, amino acid copolymer, ethylene-maleic acid copolymer, nylon, silk, and the like. Anti-FadA antibodies may be indirectly immobilized using binding agents specific for the anti-FadA antibodies (e.g., mouse antibodies specific for the FadA may be immobilized using sheep anti-mouse IgG Fc fragment specific antibody coated on the carrier or support).

The anti-FadA antibodies may be used in immunoassays. Examples of such assays are radioimmunoassays, enzyme immunoassays (e.g., ELISA), immunofluorescence, immunoprecipitation, latex agglutination, hemagglutination, and immunohistochemical (IHC) tests, which are conventional methods well-known in the art. In one example, FadA expression levels are determined using IHC. As will be appreciated by one skilled in the art, the immunoassay may be competitive or noncompetitive. Methods of detection and quantification of the signal generated by the complex formed by binding of the anti-FadA antibody with FadA will depend on the nature of the assay and of the detectable moiety (e.g., fluorescent moiety).

Alternatively, the FadA levels may be determined using mass spectrometry based methods or image (including use of labeled ligand) based methods known in the art for the detection of proteins. Other suitable methods include proteomics-based methods. Proteomics, which studies the global changes of protein expression in a sample, typically includes the following steps: (1) separation of individual proteins in a sample by electrophoresis (I-D PAGE), (2) identification of individual proteins recovered from the gel (e.g., by mass spectrometry or N-terminal sequencing), and (3) analysis of the data using bioinformatics.

Once the level of FadA and/or Fn 16S rRNA has been determined for the biological sample being analyzed, the measure level is compared to a control level, such as the level in one or more control samples. Comparison of levels according to methods described herein can be performed after the levels obtained have been corrected for both differences in the amount of sample assayed and variability in the quality of the sample used (e.g., amount of protein extracted, or amount and quality of mRNA tested). Correction may be carried out using different methods well-known in the art. For example, the protein concentration of a sample may be standardized using photometric or spectrometric methods or gel electrophoresis (as already mentioned above) before the sample is analyzed. In case of samples containing nucleic acid molecules, correction may be carried out by normalizing the levels against reference genes (e.g., housekeeping genes) in the same sample. Alternatively or additionally, normalization can be based on the mean or median signal (e.g., Ct in the case of RT-PCR) of all assayed genes or a large subset thereof (global normalization approach).

In some embodiments, comparison of FadA and/or Fn 16S rRNA expression levels obtained for a biological sample against a control level may comprise comparison of the normalized levels on a FadA and/or Fn 16S rRNA. In some embodiment, the method can include measuring Fn 16S rRNA levels and normalizing the measured Fada mRNA levels to the Fn 16s rRNA levels. An increased normalized FadA mRNA level is indicative of the subject having colorectal cancer.

In some embodiments, the subject can be identified as having colorectal cancer or an increased risk of colorectal cancer if the measure level of FadA and/or Fn 16S rRNA is at least 10%, at least 20%, at least 30%, at least 40%, at least 50%, at least 60%, at least 70%, at least 80%, at least 90%, at 100%, at least 200%, at least 300%, at least 400%, at least 500%, or more greater than the control level. In other embodiments, the subject can be identified as having colorectal cancer or an increased risk of colorectal cancer if the measure level of FadA and/or Fn 16S rRNA is at least 1 times, at least 2 times, at least 3 times, at least 4 times, at least 5 times, at least 6 times, at least times 7, at least 8 times, at least 9 times, at least 10 times or more greater than the control level. For example, a step-wise increase of FadA gene copies from the baseline of normal patients to adenomas and normal tissues adjacent to adenomas and adenocarcinomas, and to adenocarcinomas was observed with >1 log difference between each step. The biggest difference was observed between the non-cancerous controls and CRC, with >2 logs difference. The FadA mRNA levels in the colon tissues, when normalized to GAPDH, also showed a stepwise increase correlating with the FadA gene copy numbers.

The methods described can also be used to differentiate precancerous and cancer states in a subject at risk of or suspected of having colorectal cancer. In these methods, a biological sample from a subject suspected of having colorectal cancer can be obtained. The level of Fn in the biological sample can then be measured as describe herein and compared to a control level. An increased measured level compared to the control level is indicative of the subject having colorectal cancer.

Other embodiments described herein relate to a method of measuring the efficacy of a therapeutic in treating colorectal cancer in a subject. The method can include administering the therapeutic to the subject. A biological sample can be obtained from the subject after administration of the therapeutic. The level of Fn in the biological sample is measured. The measured level is compared to a control level. A decreased measured level compared to the control level is indicative of increased efficacy of the therapeutic in treating colorectal cancer in the subject.

Other embodiments described herein relate to a method of identifying a subject with increased risk of gastroinstestinal disorders, including but not limited to gastritis, inflammatory bowel disease, and/or cancer (e.g., colorectal cancer) by measuring the levels of subspecies of Fn in a bodily fluid, such as saliva and/or blood, and comparing the measured level to a control level. A difference in the measured level of the Fn subspecies compared to the control level is indicative of increased risk of colorectal cancer in the subject.

For example, we found that the five subspecies (subsp) of Fn, i.e., subsp *animalis*, subsp *fusiforme*, subsp *nucleatum*, subsp *polymorphum*, and subsp *vincentii*, are distributed differently in the saliva of normal people and patients with inflammatory bowel disease (IBD). As shown in the Example, normal individuals harbor higher levels of subsp *fusiforme* and subsp *vincentii*. These two subsp are indistinguishable based on 16S rRNA gene sequences, thus we collectively group them as "subsp *fusiforme/vincentii*". We designed primers, which can specifically detect subsp *fusiforme/vincentii*, and found that a reduced level of subsp *fusiforme* and/or *vincentii* in saliva is indicative of the subject having an increased risk of gastronintestinal disorders, such as IBD.

Still other embodiments described herein relate to a method of inhibiting *Fusobacterium nucleatum* (Fn) colonization in a subject as well as treating colorectal cancer associated with Fn colonization. The method includes administering to the subject a therapeutically effective amount of a therapeutic agent that inhibits Fn binding to or complexing with cadherin in a subject. In some embodiments, the therapeutic agent can inhibit FadA binding to E-cadherin and/or VE-cadherin.

The therapeutic agent may be used to diminish Fn colonization in the gut and elsewhere in the body, where its colonization may lead to adverse outcomes, e.g., (1) in the intrauterine cavity leading to pregnancy complications; and (2) in patients with inflammatory bowel disease. The therapeutic agent can also be used to treat colorectal cancer growth and invasion associated with Fn colonization.

The therapeutic agent (or agent) that inhibits Fn binding to or complexing with cadherin can include any composition or substance that decreases and/or suppresses the adhesion function or binding of FadA expressed by Fn to cadherin expressed by a cancer cell, epithelial cell, and/or an endothelial cell. The agent can include a targeting small molecule, polypeptide, antibody, or a fragment of an antibody, such as an Fc fused to the extracellular segment of an Ig superfamily CAM (Fc chimera), that can inhibit binding of FadA to E-cadherin and/or VE-cadherin expressed by the cancer cell, epithelial cell, and/or endothelial cell, for example, in the cancer cell microenvironment, and that can readily be administered to the subject using, for example, parenteral or systemic administration techniques (e.g., intravenous infusion).

In one aspect, the agent can include a polypeptide (or therapeutic polypeptide) that binds to and/or complexes with FadA that is expressed by Fn. The polypeptide can have an amino acid sequence that is substantially homologous to consecutive amino acids (e.g., about 10 to about 50 consecutive amino acids) of a binding portion or domain of E-cadherin and/or VE-cadherin to FadA that is expressed by a cancer cell or another cell in the cancer cell microenvironment. By substantially homologous, it is meant the polypeptide has at least about 80%, about 90%, about 95%, about 96%, about 97%, about 98%, about 99% or about 100% sequence identity with a portion of the amino acid sequence (e.g., about 10 to about 50 consecutive amino acids) of the binding portion of E-cadherin and/or VE-cadherin.

In some embodiments, the therapeutic polypeptide can consist of about 10 to about 50 amino acids and have an at least 80% sequence identity with about 10 to about 50 consecutive amino acids of EC-5 of E-cadherin or VE-cadherin and to which Fada binds. The therapeutic polypeptide can include, for example, the amino acid sequence of ASANWTIQYN (SEQ ID NO: 1) or NNFTLTDNHDN (SEQ ID NO: 2). SEQ ID NOs: 1 and 2 were found to be the minimum amino acid sequences from E-cadherin or VE-cadherin required for inhibition of FadA binding.

The therapeutic polypeptides described herein can be subject to various changes, substitutions, insertions, and deletions where such changes provide for certain advantages in its use. In this regard, therapeutic polypeptides that bind to and/or complex with FadA that is expressed by Fn can correspond to or be substantially homologous with, rather than be identical to, the sequence of a recited polypeptide where one or more changes are made and it retains the ability to function as specifically binding to and/or complexing with FadA to inhibit binding of FadA with E-cadherin and/or VE-cadherin.

The therapeutic polypeptide can be in any of a variety of forms of polypeptide derivatives and include, for example, amides, conjugates with proteins, cyclized polypeptides, polymerized polypeptides, analogs, fragments, chemically modified polypeptides, and the like derivatives.

The term "analog" includes any polypeptide having an amino acid residue sequence substantially identical to a sequence specifically shown herein in which one or more residues have been conservatively substituted with a functionally similar residue and that specifically binds to and/or complexes with FadA to inhibit binding of FadA with E-cadherin and/or VE-cadherin as described herein. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, or the substitution of one acidic residue, such as aspartic acid or glutamic acid for another.

Additionally, the therapeutic polypeptide can be made up of D-amino acids, such as D-amino acids corresponding to, for example, L-amino acids described in native SEQ ID NO: 1 and/or SEQ ID NO: 2.

The phrase "conservative substitution" also includes the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

Additional residues may also be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject polypeptide can differ by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

Any polypeptide or compound may also be used in the form of a pharmaceutically acceptable salt. Acids, which are capable of forming salts with the polypeptides, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the polypeptides include inorganic bases such as sodium hydroxide, ammonium hydroxide, potassium hydroxide and the like; and organic bases such as mono-, di- and tri-alkyl and arylamines (e.g., triethylamine, diisopropylamine, methylamine, dimethylamine and the like) and optionally substituted ethanolamines (e.g., ethanolamine, diethanolamine and the like).

The therapeutic polypeptides can be synthesized by any of the techniques that are known to those skilled in the polypeptide art, including recombinant DNA techniques. Synthetic chemistry techniques, such as a solid-phase Merrifield-type synthesis, can be used for reasons of purity, antigenic specificity, freedom from undesired side products, ease of production, and the like. A summary of the many techniques available can be found in, for example: Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., in J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

In other embodiments, the therapeutic agent, which can inhibit binding of FadA to E-cadherin and/or VE-cadherin expressed by cancer cell, epithelial cell, and/or endothelial cell, can be an antibody, such as a monoclonal antibody, a polyclonal antibody, or a humanized antibody that specifically binds to FadA binding portion of E-Cadherin and/or VE cadhering and/or the E-cadherin and/or VE-cadherin binding portion of FadA. The antibody can include Fc fragments, Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

The antibody may be an antibody that has a single heavy chain variable region and no light chain sequence. Such an antibody, called a single domain antibody (sdAb) or a nanobody, has been reported to maintain the ability to bind to an antigen (Muyldemans S. et al., Protein Eng. (1994), 7 (9), 1129-35; and Hamers-Casterman C. et al., Nature (1993), 363 (6429), 446-8). These antibodies are also encompassed in the meaning of the functional fragment of the antibody as described herein.

In some embodiments, the antibody or fragment thereof can specifically or selectively bind to SEQ ID NO: 1 or SEQ ID NO: 2 of E-cadherin and/or VE-cadherin to inhibit binding of FadA to E-cadherin and/or VE-cadherin.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. (See, for example, Kuby, Janis, Immunology, Third Edition, pp. 131-139, W.H. Freeman & Co. (1997), for a general overview of monoclonal antibody production, that portion of which is incorporated herein by reference).

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate an antibody or fragment thereof specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

In some embodiments, the therapeutic agent can include a polypeptide-Fc chimera that can specifically bind to the extracellular fragment or its receptor. Advantageously, in addition to its inhibition of cell adhesion function, the polypeptide-Fc chimera can induce immune responses, such as complement-dependent lysis and antibody-dependent cellular cytotoxicity that target tumor cells thereby eliciting anti-tumor activities. Moreover, the Fc region of the Fc chimera provides a binding site for other antibodies and promote clustering, complexing, or aggregation of multiple antibodies, which can enhance the effectiveness of the polypeptide-Fc chimera in binding to and/or complexing with the proteleolytically cleaved extracellular fragment of the Ig superfamily CAM or its receptor that is expressed by a cancer cell or another cell in the cancer cell microenvironment.

Chimeric proteins that can combine the Fc regions of IgG with one or more domains of another protein, such as various cytokines and soluble receptors, are known. These chimeric proteins can be fusions of human Fc regions and human domains of another protein. These chimeric proteins would then be a "humanized Fc chimera", which would be advantageous as a human therapeutic. (See, for example, Capon et al., Nature, 337:525-531, 1989; Chamow et al., Trends Biotechnol., 14:52-60, (1996); U.S. Pat. Nos. 5,116, 964 and 5,541,087). The chimeric protein can be a homodimeric protein linked through cysteine residues in the hinge region of IgG Fc, resulting in a molecule similar to an IgG molecule without the $C_{H1}$ domains and light chains. Due to the structural homology, such Fc fusion proteins exhibit in vivo pharmacokinetic profile comparable to that of human IgG with a similar isotype. This approach has been applied to several therapeutically important cytokines, such as IL-2 and IFN-α, and soluble receptors, such as TNF-Rc and IL-5-Rc (See, for example, U.S. Pat. Nos. 5,349,053, 6,224, 867 and 7,250,493).

In some embodiments, the polypeptide-Fc chimera is a chimeric molecule that includes a human sequence encoded polypeptide fused to a human Fc fragment and is capable of binding to or complexing with FadA that is expressed by Fn to inhibit binding of FadA to E-cadherin or VE-cadherin.

The polypeptide portion of the polypeptide-Fc chimera used for methods described herein may be a polypeptide having an amino acid sequence that is substantially homologous to about 10 to about 50 consecutive amino acids of EC-5 of E-cadherin or VE-cadherin and to which Fada binds. The polypeptide portion can include, for example, the amino acid sequence of ASANWTIQYN (SEQ ID NO: 1) or NNFTLTDNHDN (SEQ ID NO: 2).

The polypeptide portion of the polypeptide-Fc chimera, similar to the therapeutic polypeptide described above, can be subject to various changes, substitutions, insertions, and deletions where such changes provide for certain advantages in its use. In this regard, polypeptide portion correspond to or be substantially homologous with, rather than be identical to, the sequence of a recited polypeptide where one or more changes are made and it retains the ability to function as specifically binding to and/or complexing with the proteolytically cleaved extracellular portion of an Ig superfamily cell adhesion molecule.

The Fc portion of the polypeptide-Fc chimera is a domain that binds an activating Fc receptor, such as an activating Fc Ig domain and includes the hinge region that allows for dimerization. The Fc portion of the polypeptide-Fc chimera can be readily adapted to render it species-specific. For use in a murine system, e.g., cells derived from a mouse, the Fc fragment used to generate polypeptide-Fc can be that of a murine origin. In some embodiments, an Fc fragment of the murine $IgG_{2a}$ can be used.

For use in a human subject, e.g., for cancer treatment, the Fc fragment used to generate the polypeptide-Fc chimera is of a human origin. In some embodiments, the polypeptide-Fc chimera comprises an activating Fc Ig domain. Among the four human IgG isotypes, an activating Fc domain of $IgG_1$ can be used for the preparation of the polypeptide-Fc chimera.

It is appreciated that different antibody isotypes have a varying degree of cytotoxic potential in vivo (See, for example, Nimmerjahn F. & Ravetch J V., 2006, Immunity, 24:19-28). For example, the murine $IgG_{2a}$ and $IgG_{2b}$ isotypes are more efficient in clearing infections, such as bacterial infections and viral infections and in killing tumor cells than their $IgG_1$ or $IgG_3$ counterparts. This is attributable at least in part to differential ratios of activating versus inhibitory FcRs present in vivo. Similarly, with respect to human IgG isotypes, $IgG_1$ and $IgG_3$ have a stronger interaction with FcRs than $IgG_2$ or $IgG_4$. Moreover, certain polymorphic allotypes of a given isotype may influence affinity for an Fc receptor. Indeed, there are allelic variants of activating FcRs that will significantly affect the affinity for certain antibody isotypes. For example, the FcγRIIIa receptor 158V allotype displays a higher affinity for human immunoglobulin $G_1$ and increased antibody-dependent cellular cytotoxicity (Cartron G. et al., 2002, Blood, 99: 754-758).

Thus, as shall be clear to the skilled artisan, it is possible to optimize the interaction between the Fc portion of the polypeptide-Fc chimera to its corresponding Fc receptor by strategically selecting or modifying the Fc allele used for preparing the polypeptide-Fc chimera. Accordingly, a mutant or an allotype of an Fc fragment can be used here for the polypeptide-Fc chimera described herein. A number of useful mutations within an Fc domain have been described, which can affect the interaction of an Fc and its receptor, the effector function of the Fc, as well as the half-life of the Fc-containing molecule. These include specific amino acid substitutions and/or modifications to carbohydrate moieties in the Fc. (For review, see, for example, Liu et al., 2008, Immunological Reviews, 222:9-27; Nimmerjahn & Ravetch, 2007, Curr. Opin. Immunol., 19(2): 239-45).

In other embodiments, the polypeptide-Fc chimera can be engineered with an enhanced complement activity. Generally, complement can be activated by at least three pathways, leading to the formation of the membrane attack complex (MAC) C5b-9, which forms pores in the plasma membranes of target cells and causes their lysis. C1q binding to the Fc domain is a critical step in this process. Among the human IgG subclasses, only $IgG_1$ and $IgG_3$ can initiate the complement cascade. In some embodiments, mutations are introduced to the Fc domain of the polypeptide-Fc chimera, so as to promote C1q recruitment and the C1q-Fc interaction. The residues of the Fc targeted for such mutations include, but are not limited to: Asp270, Lys322, Pro329 and Pro331. These mutations involve substituting the corresponding residue(s) with nonpolar neutral amino acids, such as Ala, Met, or Trp. In a specific embodiment, the polypeptide-Fc contains the mutation, Lys326Trp, Glu333Ser or both.

In addition, it should be noted that when chimeric or fusion proteins with artificial sequences and activities are used as therapeutic agents, in some circumstances, patients treated with such a chimeric or fusion protein trigger an unwanted immune response, such as development of antibodies against the agent. Certain structural modifications of an Fc fragment have been shown to reduce immunogenicity of a therapeutic fusion protein. See, for example, U.S. Pat. No. 6,992,174 B2, which is incorporated by reference herein; Liu et al., 2008, Immunological Reviews, 222:9-27. Such modifications may be useful for an effective design of the polypeptide-Fc chimera described herein.

The polypeptide-Fc chimera used in the methods may include a linking moiety that connects the polypeptide portion with an Fc fragment. In some cases, a hinge region of Fc fusion protein molecules serves as a spacer between the Fc region and the fused polypeptide (e.g., soluble receptor), allowing these two parts of the molecule to function separately.

In some embodiments, the Fc portion and the polypeptide portion that comprise a chimeric molecule are linked via a linking molecule which is not a contiguous portion of either the polypeptide or Fc portions and which covalently joins an amino acid of the polypeptide to an amino acid of Fc. As used herein, a linking molecule that is "not a contiguous portion" means that the polypeptide portion and the Fc portion of the chimera are connected via an additional element that is not a part of the polypeptide or immunoglobulin that is contiguous in nature with either of the chimeric portions and functions as a linker.

In some embodiments, the linking molecule may be a peptide linker. Where the linker is a peptide linker, the polypeptide-Fc chimera may be produced as a single recombinant polypeptide using a conventional molecular biological/recombinant DNA method.

In other embodiments, a flexible peptide linker can be used. A flexible peptide linker can be about 20 or fewer amino acids in length. For example, a peptide linker can contain about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

Alternatively, a linking molecule may be a non-peptide linker. As used herein, a non-peptide linker useful for the method described herein is a biocompatible polymer including two or more repeating units linked to each other. Examples of the non-peptide polymer include but are not limited to: polyethylene glycol (PEG), polypropylene glycol (PPG), co-poly (ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, and heparin. For more detailed descriptions of non-peptide linkers useful for Fc fusion molecules, see, for example, WO/2006/107124, which is incorporated by reference herein. Typically such linkers will have a range of molecular weight of about 1 kDa to 50 kDa, depending upon a particular linker. For example, a typical PEG has a molecular weight of about 1 to 5 kDa, and polyethylene glycol has a molecular weight of about 5 kDa to 50 kDa, and more preferably about 10 kDa to 40 kDa.

Molecular biological and biochemical techniques for preparing an Fc chimera are known. In some embodiments, the polypeptide-Fc chimera can be produced by conventional recombinatory DNA methods. In other embodiments, the polypeptide-Fc chimera can be produced as a single (e.g., contiguous) recombinant polypeptide. In still other embodiments, two or more portions of the polypeptide-Fc can be produced as separate fragments and are subsequently linked together to yield the polypeptide-Fc chimera. For example, the polypeptide portion of the polypeptide-Fc chimera and an Fc portion of the polypeptide-Fc chimera can each be produced as separate recombinant polypeptides then fused together by a chemical linking means to yield the polypeptide-Fc. This production methodology may be preferred particularly in situations where a non-peptide linking molecule is employed. Similarly, this production methodology may be also preferred if a chimeric polypeptide-Fc does not fold correctly (e.g., does not properly bind a ligand) when made as a single contiguous polypeptide.

For the production of recombinant polypeptides, a variety of host organisms may be used. Examples of hosts include, but are not limited to: bacteria, such as *E. coli*, yeast cells, insect cells, plant cells and mammalian cells. Choice of a host organism will depend on the particular application of the polypeptide-Fc chimera. The skilled artisan will understand how to take into consideration certain criteria in selecting a suitable host for producing the recombinant polypeptide. Factors affecting selection of a host include, for example, post-translational modifications, such as phosphorylation and glycosylation patterns, as well as technical factors, such as the general expected yield and the ease of purification. Host-specific post-translational modifications of the polypeptide-Fc chimera, which is to be used in vivo, should be carefully considered because certain post-translational modifications are known to be highly immunogenic (antigenic).

In certain aspects, the therapeutic agent can be directly or indirectly labeled with a detectable moiety to allow the therapeutic agent to be used for diagnostic purposes. The detectable moiety can facilitate detection of the therapeutic agent allowing visualization of the complex formed by binding of the therapeutic agent to FadA of the bacteria. The detectable moiety can be selected such that it generates a signal, which can be measured and whose intensity is related (preferably proportional) to the amount of the molecular probe bound to the tissue being analyzed. Methods for labeling biological molecules, such as polypeptides and antibodies are well-known in the art.

In some embodiments, the therapeutic agent with the detectable moiety when used in the methods described herein can be detected upon administration to the subject to measure the efficacy of the therapeutic agent in treating the cancer in the subject. For example, a therapeutically effective amount of an agent that specifically binds to or complexes with FadA and that includes a detectable moiety can be administered to the subject to treat the cancer. The therapeutic agent bound to and/or complexed with the FadA can then detected in the subject to provide the location and/or distribution of Fn in the subject. The distribution of Fn may be correlated with the presence or absence of cancer cells in the tissue. A distribution may be dispositive for the presence or absence of a cancer cells or may be combined with other factors and symptoms by one skilled in the art to positively detect the presence or absence of cancer cells. The location and/or distribution of Fn and the cancer cells in subject can be monitored over time by subsequent administrations of the therapeutic agent to determine efficacy of the therapeutic agent in treating the cancer. A reduction, for example, in cancer volume, growth, migration, and/or dispersal in a subject may be indicative of the efficacy of a given therapeutic agent. This can provide a direct clinical efficacy endpoint measure of the therapeutic.

In some embodiments, the therapeutic agents can be provided in a pharmaceutical composition. The pharmaceutical compositions can include a pharmaceutically effective amount of a therapeutic agents described above and a pharmaceutically acceptable diluent or carrier.

The term "pharmaceutically acceptable carrier", "diluents", "adjuvant" and "physiologically acceptable vehicle" and the like are to be understood as referring to an acceptable carrier or adjuvant that may be administered to a patient, together with an agent of this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

In addition, the term "pharmaceutically effective amount" or "therapeutically effective amount" refers to an amount (dose) effective in treating a patient, having, for example, cancer, such as glioblastoma multiforme. It is also to be understood herein that a "pharmaceutically effective amount" may be interpreted as an amount giving a desired therapeutic effect, either taken into one dose or in a dosage or route or taken alone or in combination with other therapeutic agents. A "pharmaceutically effective amount" may be understood as an amount of the therapeutic agent that is effective to that decreases and/or suppresses the cell adhesion function of the proteolytically cleaved extracellular fragment.

Determination of a therapeutically effective amount is within the capability of those skilled in the art. The exact formulation, route of administration and dosage can be chosen by the individual physician in view of the patient's condition.

Pharmaceutical compositions described herein can be administered in a suitable pharmaceutical carrier by one of several routes, which include direct injection, and topical application. Formulations of the compositions will vary according to the route of administration selected (e.g., solution or emulsion).

In one embodiment, the therapeutic agent described herein can be administered to a cancer cell, e.g., colorectal cancer cell, of a subject by contacting the cell of the subject with a pharmaceutical composition described above. In one aspect, a pharmaceutical composition can be administered directly to the cell by direct injection. Alternatively, the pharmaceutical composition can be administered to the subject systematically by parenteral administration, e.g., intravenous administration).

In a further example, the therapeutic agent can be used in combination and adjunctive therapies for inhibiting cancer cell proliferation, growth, and motility. The phrase "combination therapy" embraces the administration of a therapeutic agent, which inhibits binding of FadA to E-cadherin and/or VE-caherin that is expressed by a cancer cell or another cell in the cancer cell microenvironment, and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). The phrase "adjunctive therapy" encompasses treatment of a subject with agents that reduce or avoid side effects associated with the combination therapy of this application.

A combination therapy is intended to embrace administration of these therapeutic agents in a sequential manner, that is, wherein different therapeutic agents are administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of therapeutic agents can be effected by an appropriate routes including, but not limited to, oral routes, intravenous routes, intramuscular routes, and direct absorption through mucous membrane tissues. The therapeutic agents can be administered by the same route or by different routes. The sequence in which the therapeutic agents are administered is not narrowly critical.

Combination therapy also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at a suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the therapeutic agent, which inhibits binding of FadA to E-cadherin and/or VE-caherin that is expressed by a cancer cell or another cell in the cancer cell microenvironment, can be administered in combination at least one anti-proliferative agent selected from the group consisting of a chemotherapeutic agent, an antimetabolite, an antitumorgenic agent, an antimitotic agent, an antibacterial agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Other embodiments described herein relating to a method of treating a subject having or suspected of having a gastrointestinal disorder, such as IBD, gastritis, and/or colorectal cancer, can include first obtaining a sample or biopsy of cells and/or tissue having or suspected of having Fn from the subject. The biopsied cells and/or tissue is then assayed to determine if the biopsied cells and/or tissue includes elevated levels of Fn and/or FadA compared to a control level. In some embodiments, the sample or biopsy from the subject can be assayed by measuring the Fn 16S RNA and/or FadA mRNA levels in the sample or biopsy using, for example, qPCR techniques.

Detection of elevated Fn and/or FadA levels in the sample or biopsy can be indicative that the subject has a gastrointestinal disorder associated with Fn colonization, and that treatment of the subject with an amount of a therapeutic agent described herein that inhibits binding of FadA to E-cadherin and/or VE-cadherin can have efficacy or enhanced efficacy in inhibiting and/or reducing gastrointestinal disorder. In contrast, absence of elevated Fn and/or FadA levels in the sample or biopsy is indicative that the subject does not have gastrointestinal disorder associated with Fn colonization and that treatment of the subject with a therapeutically effective amount of a therapeutic agent described herein that inhibits binding of FadA to E-cadherin and/or VE-cadherin will have reduced efficacy or little if any efficacy in inhibiting and/or reducing the gastrointestinal disorder in the subject.

The following Example is included to demonstrate different embodiments of the invention. It should be appreciated by those of skill in the art that the techniques disclosed in the examples, which follow represent techniques discovered by the inventor to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

Example

In this Example, we demonstrate that FadA binds to E-cadherin on CRC and non-CRC cells, mediating Fn attachment of and invasion into the cells. FadA modulates E-cadherin and activates β-catenin signaling, leading to increased expression of transcription factors, oncogenes, Wnt genes, and inflammatory genes, as well as growth stimulation of CRC cells. Further, we show that while FadA binding to CRC cell is sufficient to turn on the Wnt and oncogenes, its internalization mediated by clathrin is needed to activate the inflammatory genes. This Example unveils a novel mechanism of Fn in CRC and identifies FadA as a diagnostic and therapeutic target for CRC.

Bacterial Strains, Cell Cultures, Construction of Plasmids, Protein Purification and GST Pull-Down Assays Bacteria and human cell lines were cultured as previously described. EC domains of E-cadherin were amplified by PCR from pcDNA3-E-cadherin (AddGene, MA) vector using primers listed in Table 1.

TABLE 1

| Primers | Sequence 5'-3'* | Purpose |
| --- | --- | --- |
| CDH1-EC1-F-SalI | GGCC GTCGACGACTGGGTTATTCCTCCCAT (SEQ ID NO: 3) | Cloning of CDH1 EC1-2 and 1-3 domain |
| CDH1-EC2-F-EcorI | GGCC GAATTC ACCCAGGAGGTCTTTAAGGG (SEQ ID NO: 4) | Cloning of CDH1 EC2-3 domain |
| CDH1-EC2-R-NotI | GGCC GCGGCCGCTTAGAAGATCGGAGGATTATCGT (SEQ ID NO: 5) | Cloning of CDH1 EC1-2 domain |
| CDH1-EC3-F-EcorI | GGCC GAATTC AATCCCACCACGTACAAGGG (SEQ ID NO: 6) | Cloning of CDH1 EC3-4 domain |
| CDH1-EC3-R-NotI | GGCC GCGGCCGCTTAAAAGATGGGGGCTTCATTCA (SEQ ID NO: 7) | Cloning of CDH1 EC1-3 domain |
| CDH1-EC4-F-EcorI | GGCC GAATTC GTGCCTCCTGAAAAGAGAGT (SEQ ID NO: 8) | Cloning of CDH1 EC4-5 and EC4 domain |
| CDH1-EC4-R-XhoI | GGCC CTCGAG TTAGGGGGCGTTGTCATTCACAT (SEQ ID NO:9) | Cloning of CDH1 EC3-4 and EC4 domain |
| CDH1-EC5-F-EcorI | GGCC GAATTC ATACCAGAACCTCGAACTAT (SEQ ID NO: 10) | Cloning of CDH1 EC5 domain |
| CDH1-EC5-R-XhoI | GGCC CTCGAG TTACTTCCTACAGACGCCAGCGG CDH1 EC4-5 (SEQ ID NO: 11) | Cloning of and EC5 domain |
| CDH1-Cyto F-EcorI | GGCC GAATTC CTTGCTTTGCTAATTCTGAT (SEQ ID NO: 12) | Cloning of CDH1 intracellular domain |
| CDH1 Cyto R-XhoI | GGCC CTCGAG TTAGTCGTCCTCGCCGCCTCCGT (SEQ ID NO: 13) | Cloning of CDH1 intracellular domain |
| CDH1-del-1-F | ATCATTGATGCAGACCTTCC (SEQ ID NO: 14) | Construction of GST-CDH1 EC5 domain Δ1 |
| CDH1-del-1-R | GAATTCCGGGGATCCCAGGG (SEQ ID NO: 15) | Construction of GST-CDH1 EC5 domain Δ1 |
| CDH1-del-2-F | ACACACGGGGCGAGTGCCAA (SEQ ID NO: 16) | Construction of GST-CDH1 EC5 domain Δ2 |
| CDH1-del-2-R | GTTTATGACCTGAGGCTTTG (SEQ ID NO: 17) | Construction of GST-CDH1 EC5 domain Δ2 |
| CDH1-del-3-F | ACACACGGGGCGAGTGCCAA (SEQ ID NO: 18) | Construction of GST-CDH1 EC5 domain Δ3 |
| CDH1-del-3-R | TAGTTCTGCTGTGAAGGGAG (SEQ ID NO: 19) | Construction of GST-CDH1 EC5 domain Δ3 |
| WNT7A-F | GACGCCATCATCGTCATAGGA (SEQ ID NO: 20) | qPCR |
| WNT7A-R | GGCCATTGCGGAACTGAA (SEQ ID NO: 21) | qPCR |
| WNT7B-F | TGAAGCTCGGAGCACTGTCA (SEQ ID NO: 22) | qPCR |
| WNT7B-R | GGCCAGGAATCTTGTTGCA (SEQ ID NO: 23) | qPCR |
| WNT9A(14)-F | GGGCAGACGGTCAAGCAA (SEQ ID NO: 24) | qPCR |

TABLE 1-continued

| Primers | Sequence 5'-3'* | Purpose |
|---|---|---|
| WNT9A(14)-R | CCAGCCTTGATCACCTTCACA (SEQ ID NO: 25) | qPCR |
| WNT10A-F | CTGGGTGCTCCTGTTCTTCCTA (SEQ ID NO: 26) | qPCR |
| WNT10A-R | GAGGCGGAGGTCCAGAATG (SEQ ID NO: 27) | qPCR |
| WNT10B-F | CCTCGCGGGTCTCCTGTT (SEQ ID NO: 28) | qPCR |
| WNT10B-R | AGGCCCAGAATCTCATTGCTTA (SEQ ID NO: 29) | qPCR |
| MYC-F | CCTAGTGCTGCATGAGGAGA (SEQ ID NO: 30) | qPCR |
| MYC-R | TCTTCCTCATCTTCTTGCTCTTC (SEQ ID NO: 31) | qPCR |
| CDC1-F | TGCCCTCTGTGCCACAGATG (SEQ ID NO: 32) | qPCR |
| CDC1-R | TCTGGAGAGGAAGCGTGTGA (SEQ ID NO: 33) | qPCR |
| Clathrin-F | AACGGTCCTGCTGATGGCTA (SEQ ID NO: 34) | qPCR |
| Clathrin-R | ATCCAGCTCTTGCAGCCGTT (SEQ ID NO: 35) | qPCR |
| PTK-6-F | CGGAACCGTGGTTCTTTG (SEQ ID NO: 36) | qPCR |
| PTK-6-R | ACTCGGCTTCTCGCTGAC (SEQ ID NO: 37) | qPCR |
| GAPDH-F | TGCACCACCAACTGCTTAG (SEQ ID NO: 38) | qPCR |
| GAPDH-R | GATGCAGGGATGATGTTC (SEQ ID NO: 39) | qPCR |
| T-bac-F | ACTCCTACGGGAGGCAGCAG (SEQ ID NO: 40) | qPCR |
| T-bac-R | ATTACCGCGGCTGCTGG (SEQ ID NO: 41) | qPCR |
| T-Fn-F | CTTAGGAATGAGACAGAGATG (SEQ ID NO: 42) | qPCR |
| T-Fn-R | TGATGGTAACATACGAAAGG (SEQ ID NO: 43) | qPCR |
| FadA-F | GAAGAAAGAGCACAAGCTGA (SEQ ID NO: 44) | qPCR |
| FadA-R | GCTTGAAGTCTTTGAGCTCT (SEQ ID NO: 45) | qPCR |

*Sites for restrictive endonucleases are underlined

Tissue Culture Attachment and Invasion Assays

Cells were seeded in 24-well or 96-well plates at $8 \times 10^4$ cells or $2.5 \times 10^4$ cells per well in the growth medium and grown to 100% confluent. Bacteria were added to the cells at a multiplicity of infection (MOI) of 50. Following 1 hr incubation at 37° C. in 5% $CO_2$, the monolayers were washed 3 times with D-PBS, pH 7.1, supplemented with $Ca^{2+}$ and $Mg^{2+}$. Cells were lyzed with water for 20 min at 37° C. Serial dilutions of the lysates were plated onto blood agar plates to enumerate the total cell-associated bacteria. For invasion assays, the bacteria were incubated with the monolayers at 37° C. for 4 hrs, followed by washes with PBS. Fresh media containing 300 μg/ml gentamicin and 200 μg/ml metronidazole were added to the monolayers and incubated for an additional hour to kill extracellular bacteria. The cells were then washed and lyzed with water as described above. The levels of attachment and invasion were expressed as the percentage of bacteria recovered following cell lysis relative to the total number of bacteria initially added. Each experiment was performed in triplicates and repeated at least twice.

Antibodies, Peptides, and Western Blot Analysis

The following antibodies were used: anti-FadA monoclonal antibody (mAb) 5G11-3G8 (Xu et al., 2007), mAb anti-CDH1 (Abcam or Cell Signaling Tech), polyclonal anti-phospho-CDH1 (ECM Biosciences), mAb anti-GAPDH (Invitrogen), mAb anti-β-catenin (R&D systems), polyclonal anti-phospho-β-catenin (Cell Signaling Tech), mAb anti-LEF/TCF1 (Invitrogen), mAb anti-NFkB (Invitrogen), mAb anti-Myc (Cell Signaling Tech), mAb anti-cyclin D1 (Cell Signaling Tech), mAb anti-EGFR (Cell Signaling Tech), mAb anti-GAPDH (Cell Signaling Tech), mAb anti-PCNA (Cell Signaling Tech), polyclonal goat-anti-mouse or goat-anti-rabbit secondary antibody conjugated with horseradish peroxidase (HRP) (Pierce Biotechnology). Peptides were synthesized by Neo Group, Inc (Cambridge, Mass.). Western blot analyses were performed as previously described.

Co-Immunoprecipitation (Co-IP) Assay

500 μg of HEK293 cell lysate prepared with CO-IP Lysis/Wash Buffer (Pierce) were mixed with 100 μg of BSA or *E. coli* lysate expressing FadAc or mFadA, followed by the addition of mouse monoclonal anti-CDH1 antibodies. The protein complex was captured by agarose A/G beads (Santa Cruz) as previously described, followed by elution and Western blot analysis. An equal volume of the elutes were loaded onto SDS-PAGE.

DNA and siRNA Transfection

CDH1 transfections were performed as previously described. siRNA assays were performed using the Flexi-Tube siRNA anti-CDH1 or anti-beta-catenin reagent and All Stars FlexiTube Control siRNA from Qiagen (Valencia, Calif.) according the manufacturer's instructions.

Cell Proliferation Assay

CRC cells were seeded in 24-well plates at 1×10⁴ cells per well in the growth medium. Cells were untreated, or incubated with FadAc or peptides at indicated concentration, or with bacteria at a multiplicity of infection (MOI) of 1000:1. Cell numbers were counted at 24-hour intervals using a hemocytometer. Each experiment was performed in triplicates and repeated at least twice.

Preparation of Subcellular Fractions

Cells were incubated with 1 mg/ml of FadAc or mFadA followed by the extraction of subcellular fractions. When indicated, 50 µM of the corresponding protein tyrosine kinase inhibitor (Genistein) and clathrin inhibitor (Pitstop2) were pre-incubated with cells for 1 hour. Membrane, cytosolic and nuclei fractions were prepared using the Compartmental Protein Extraction kit (Millipore) according to the manufacturer's instructions.

Luciferase Reporter Assay

HCT116 cells were seeded in 96-well plates at 2.5×10⁴ cells per well in the growth medium and grown to 100% confluent. Cells were transfected with 0.2 µg of TOPFlash, a luciferase reporter vector carrying TCF promoter upstream of the luciferase gene and can be activated by β-catenin, or FOPFlash (with mutations rendering insensitivity to β-catenin activation), using Lipofectamine 2000 (Invitrogen) according to the manufacturer's instructions. On the following day, cells were treated with bacteria at a multiplicity of infection (MOI) of 1000:1 for 2 hours. Reporter assays were performed using the luciferase reporter system (Promega, Madison, Wis.). The experiment was performed in triplicates and repeated twice.

Immunofluorescent and Immunohistochemical (IHC) Staining

Immunofluorescent staining of cells was performed as previously described. Mouse anti-β-catenin mAb and Alexa Fluor 634-conjugated goat anti-mouse polyclonal antibodies were used. IHC analysis of xenograft tumors were performed as previously described, using rabbit anti-Fn polyclonal antibodies. Pre-immune serum from the same rabbit was used as control.

Xenografts

The animal protocol was approved by the Case Western Reserve University Institutional Animal Care and Use Committee. An inoculum of 5×10⁶ cells were injected s.c. and bilaterally into 4- to 6-week-old female nude mice (5 per group) as previously described. The mice were randomized to receive one of the following: FadAc or mFadA (each at 80 µg), BSA (0.01 µmol, i.e., 660 µg), or peptide (0.01 µmol), or bacteria at 1×10⁷ cfu, at each inoculation site.

Clinical Specimens

This study was approved by the University Hospitals of Cleveland Institutional Review Board. A total of 19 cases diagnosed with colonic adenocarcinoma and 16 cases of adenomas were retrieved from files at the Department of Pathology, University Hospitals Case Medical Center, Cleveland, Ohio. H&E slides were reviewed to confirm the presence of adenocarcinoma (or adenoma). A representative block of colon adenocarcinoma (or adenoma) and a block of normal colon from the same patient were used. In addition, normal colon tissues were derived from 14 individuals undergoing resection for benign colon pathology or resection of adjacent organs. Exclusion criteria were history of gastrointestinal malignancies, presence of prominent inflammation or abscess, and history of inflammatory bowel disease. All cases were from within the last 12 months. Genomic DNA was extracted from formalin-fixed paraffin-embedded tissue samples as previously described. RNA was extracted using PureLink FFPE Total RNA Isolation Kit (Invitrogen) or RNeasy FFPE Kit (Qiagen).

Real-Time Quantitative PCR (qPCR)

Total RNA was extracted from CRC cells, xenografts, or clinical specimens. cDNA synthesis and RT-PCR were performed as previously described, using primers listed in Table 1. Data were analyzed by the ΔΔCt method and normalized to the GAPDH or Fn-specific 16S rRNA. To quantify the fadA gene copies, plasmid carrying fadA was serially diluted to $10^2$-$10^8$ fadA copies/µl and used to generate standard curves for Ct values. The fadA gene copies in the clinical samples were calculated based on the standard curves. Each experiment was performed in triplicates and repeated at least three times.

Statistical Analysis

The differences between groups were examined by two-tailed one-way analysis of variance (ANOVA) followed by Student-Newman-Keuls (SNK) test. For the clinical specimens the Kruskal-Wallis non-parametric test was performed followed by Conover test. $p<0.05$ were considered statistically significant.

Results

Fn Stimulates Human CRC Cell Proliferation

Wild-type Fn 12230 significantly stimulated proliferation of human colon cancer cells HCT116, DLD1, SW480, and HT29, but only weakly stimulated RKO. It did not stimulate the non-CRC cells HEK293. Compared to the untreated cells or those incubated with E. coli DH5α, the growth stimulation increased by approximately 100% for HCT116, DLD1, SW480, and HT29, but only 18% for RKO, after 72 hours (FIG. 1A). The fadA-deletion mutant US1 weakly stimulated the growth of all cancer cell lines. The fadA-complementing clone, USF81, restored proliferation of HCT116, DLD1, SW480, and HT29 to the wild-type level. Furthermore, HCT116 growth was enhanced by purified FadAc in a dose-dependent manner, with the maximum stimulation observed at 1 mg/ml, while mFadA exhibited no stimulatory effect (FIG. 1B). Neither FadAc or mFadA stimulated growth of RKO. These results indicate that stimulation of CRC cell by Fn is FadA-dependent.

FadA Binds to E-Cadherin on CRC Cells

To investigate the mechanism by which FadA stimulates CRC cell growth, we set out to identify CRC cell receptors for FadA. It was previously shown that FadA binds to VE-cadherin on endothelial cells. Cadherins are a large family of calcium-dependent cell adhesion glycoproteins, each composed of five extracellular repeat domains (EC1-EC5), a transmembrane domain, and a highly conserved cytoplasmic tail that binds other cytoplasmic components including β-catenin (FIG. 2A). Given the 33.5% similarity between VE- and E-cadherins, we speculated if FadA also bound to E-cadherin. E-cadherin is present on epithelial cells, including the non-cancerous HEK293, as well as the CRC cells, except RKO (FIG. 2B). FadA binding to E-cadherin was directly tested by co-immunoprecipitation. FadAc co-precipitated with E-cadherin, while mFadA did not (FIG. 2C). Using the GST pull-down assay, we determined that FadAc bound specifically to EC5 of E-cadherin, but not to EC1-4, the transmembrane, or the cytoplasmic domains (FIG. 2D). Deletions of various regions in EC5 showed that region 3 was responsible for FadA binding.

FadA Promotes Fn Attachment and Invasion of E-Cadherin-Expressing Cells

Attachment and invasion are hallmarks of Fn. Thus, we tested the role of FadA binding to E-cadherin in these processes. Fn attachment and invasion of non-CRC cells HEK293 was inhibited by mouse monoclonal antibody HECD-1 raised against the extracellular domain of E-cadherin. Deletion of fadA (US1) severely impaired the ability of Fn to bind and invade HEK293, whereas the fadA-complemented clone, USF81, restored the activities. Down-regulation of E-cadherin expression by siRNA in HEK293 significantly inhibited attachment and invasion by wild-type Fn and USF81. These results indicate that Fn attachment and invasion of HEK293 requires FadA and E-cadherin.

Similar observations were made with CRC cells HCT116 expressing E-cadherin. US1 (fadA−) was defective in attachment and invasion of HCT116, compared to wild-type Fn or USF81 (fadA+) (FIG. 3A). Inhibition E-cadherin expression by siRNA reduced attachment and invasion (FIG. 3A). In contrast, no difference was observed among Fn 12230, US1 and USF81 in their weak binding and invasion of the non-E-cadherin-expressing RKO cells (FIG. 3B). Transfection of RKO with the full-length E-cadherin led to increased binding and invasion by Fn 12230 and USF81 to levels comparable to those observed in HCT116 (FIG. 3B). These results indicate that FadA mediates Fn attachment and invasion of CRC cells via E-cadherin.

E-cadherin can be internalized via clathrin. Pitstop2, a clathrin inhibitor, prevented Fn invasion of HCT116, without affecting attachment (FIG. 3C). Fn stimulated expression of the inflammatory genes including NF-kappaB and cytokines IL-6, 8, and 18 from HCT116 (FIG. 3D). Such stimulation was abolished in the presence of the clathrin inhibitor, indicating that invasion was required for the stimulation of inflammation (FIG. 3D).

Identification of Inhibitory Peptides to Prevent Fn Attachment and Invasion

Since FadA bound to the EC5 domain of E-cadherin, we tested the role of EC5 in Fn attachment and invasion. Fn attachment and invasion of HCT116 was inhibited by purified GST-EC5 fusion protein in a dose-dependent manner, with maximum inhibition observed at 0.1 µM (FIGS. 4A & 4B). Synthetic peptides derived from different regions of EC5 were then tested for their ability to inhibit Fn attachment and invasion (FIGS. 4A & 4C). Peptide 3, corresponding to region 3, exhibited similar inhibitory effect as EC5 (compare FIGS. 4B & 4C). To determine the minimal sequences required for inhibition, sequential deletions of peptide 3 were generated. The results showed that the 11-aa peptide (ASANWTIQYND) (SEQ ID NO: 64) was the minimum required, and was designated as the "inhibitory peptide" (IP) (FIG. 4D).

FadA Promotes CRC Cell Proliferation Via E-Cadherin

Stimulation of HCT116 growth by Fn was inhibited by the CDH1-specific siRNA, EC5, and the inhibitory peptide (FIG. 1C). In the non-E-cadherin-expressing RKO cells, transfection of the full-length E-cadherin resulted in growth stimulation by Fn (FIG. 1D). As in HCT116, such stimulation was diminished by EC5 and the inhibitory peptide (FIG. 1D). Similar observations were made using purified FadAc instead of Fn. These results elucidate the critical role of E-cadherin in promoting CRC cell growth.

FadAc Activates E-Cadherin-Mediated Cellular Signaling

To investigate the downstream events subsequent to FadA binding to E-cadherin, HCT116 were fractionated following incubation with purified FadA. FadAc, but not mFadA, bound to the HCT116 membranes within five minutes of incubation, leading to E-cadherin phosphorylation on the membrane and internalization (FIG. 5A). This was accompanied by decreased phosphorylation of β-catenin, β-catenin accumulation in the cytoplasma and translocation into the nucleus, resulting in activation of β-catenin-regulated transcription (CRT), as evidenced by increased expression of transcription factors lymphoid enhancer factor (LEF)/T-cell factor (TCF), NF κB, and oncogenes Myc and Cyclin D1 (FIG. 5A). It was previously shown that protein tyrosine kinase plays a crucial role in E-cadherin endocytosis and recycling. Interestingly, the protein tyrosine kinase (PTK) inhibitor, Genistein, not only prevented E-cadherin phosphorylation and internalization, but also abolished FadA binding to the membranes and its internalization, as well as the above-described CRT activation (FIG. 5A). These results suggest that phosphorylation of E-cadherin or other cellular components are required for activation of CRT. FadA may bind to phosphorylated E-cadherin, or it may bind to non-phosphorylated E-cadherin, which is then phosphorylated leading to positive feedback. The central role of β-catenin in regulating the cellular responses was confirmed using HCT116 β-catenin$^{−/−}$ cells, which did not affect FadA binding to E-cadherin, phosphorylation of E-cadherin, or the internalization, but prevented all gene activations tested in the nuclei (FIG. 5A).

The clathrin inhibitor, although did not affect FadA binding to or E-cadherin phosphorylation on the membranes, inhibited FadA and E-cadherin internalization. A surprise consequence was the divergent responses observed in the nuclei. Translocation of β-catenin and expression of LEF/TCF, Wnt and oncogenes were unaffected. In contrast, no NF kappaB activation was observed (FIG. 5A). These results indicate that tumor growth and inflammatory responses, although both requiring β-catenin, are differentially regulated.

The Western blot analysis of protein levels were corroborated with real-time quantitative PCR (qPCR) analysis of the mRNA levels (FIG. 5b-5E). While PTK inhibitor and CDH1-specific siRNA inhibited activation of tumor growth and inflammatory genes, the clathrin inhibitor only inhibited the inflammatory genes, but not the Wnt or oncogenes.

To further confirm the role of FadA in CRT activation, we performed confocal microscopy analysis and observed nuclei translocation of β-catenin in HCT116 in response to wild-type Fn, but not to US1 (fadA−) (FIG. 5F). In addition, wild-type Fn and USF81 (fadA+), but not US1 (fadA−), activated the luciferase reporter gene in TOPFlash carrying the β-catenin-response promoter, but not in FOPFlash carrying β-catenin-non-response promoter (FIG. 5G).

FadA Promotes E-Cadherin-Mediated CRC Tumor Growth and Induction of Pro-Inflammatory Cytokines in Xenograft Mice To examine the effects of FadA and Fn on CRC cell growth in vivo, HCT116 were inoculated into nude mice, followed by treatment with either purified protein or bacteria. Tumor growth was increased by 20% after 3 weeks of treatment by FadAc, compared to those treated with mFadA or BSA (FIGS. 6A and 6D). No increase was detected in the presence of 0.01 µmol inhibitory peptide, but not the control peptide, indicating the role of FadA binding to E-cadherin in tumor growth (FIGS. 6B and 6D). FadAc had no stimulatory effect on the non-E-cadherin-expressing RKO (FIG. 6C).

When wild-type Fn was injected into HCT116 xenografts, abscess formation was observed within 3-5 days (data not shown). Immunohistochemical analysis using anti-Fn antibodies showed that wild-type Fn invaded into the tumor tissues while US1 (fadA−) did not (FIG. 6E). Nor did *E. coli* DH5α (data not shown). Fn invasion was prevented by the inhibitory peptide, but not by the control peptide (FIG. 6E). FadA and wild-type Fn (FIG. 6F) stimulated the tumor growth genes and the inflammatory genes to same extent, which were inhibited by the inhibitory peptide, but not the control peptide, consistent with the observations in vitro.

Patients with CRC and Precancerous Adenomas have Elevated FadA Gene and Expression Levels Compared to Normal Individuals We examined FadA gene and expression levels in human colon specimens from the following 5 groups: (1) normal non-cancerous individuals (n=14), (2) normal tissues from patients with precancerous adenomas (n=16); (3) precancerous adenomas (n=16); (4) normal tissues from patients with adenocarcinomas (n=19); and (5) adenocarcinomas (n=19). A step-wise increase of FadA gene copies was observed from Group 1 to Group 2-4, and to Group 5, with >1 log difference between each step (FIG. 7A). The biggest difference was observed between the non-cancerous controls and CRC, with >2 logs difference (FIG. 7A). The FadA mRNA levels in the colon tissues, when normalized to GAPDH, also showed a stepwise increase correlating with the FadA gene copy numbers (data not shown). When the FadA mRNA levels were normalized to Fn 16S RNA to reflect FadA expression in Fn, a significance increase was only observed in the carcinoma tissues (Group 5), indicating Fn exhibits increased virulence in CRC, compared to the normal and precancerous tissues (FIG. 7B). Consistent with the increase of FadA, expression of a representative Wnt gene, Wnt7b, and a representative inflammatory gene, NF 032, were also significantly increased in CRC, corroborating with the results obtained in vitro and in xenograft mice.

Figure 8B:
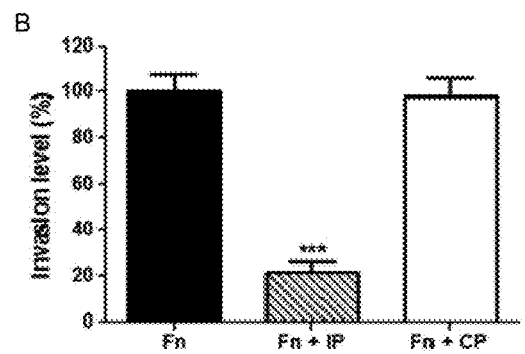

Inhibitory Peptide (IP) Blocks *Fusobacterium nucleatum* (Fn) Attachment and Invasion of Endothelial Cells As illustrated in FIG. 8, we found that the inhibitory peptide (IP) could be used to block *Fusobacterium nucleatum* (Fn) attachment and invasion of endothelial cells. Thus, the inhibitory peptide has much broader usage than just preventing Fn binding to the colorectal cancer cells. It has the potential to be used to prevent systemic dissemination of Fn.

Figure 9A:
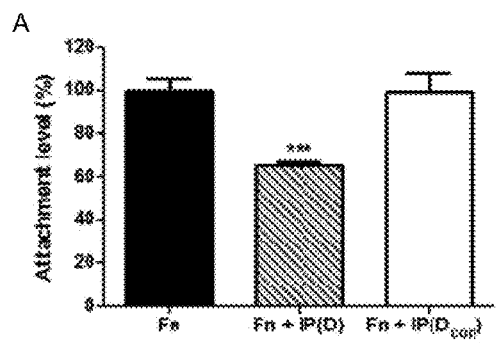
FIG. 9 illustrates (A) inhibition Fn binding to HCT116 cells by inhibitory peptide made up of D-amino acids [IP(D)] in the reverse sequence as the L-amino acid IP. (B) "IP(D$_{con}$)" is a D-amino acid peptide in the same order as the L-amino acid IP, serving as negative control.
Figure 9B:
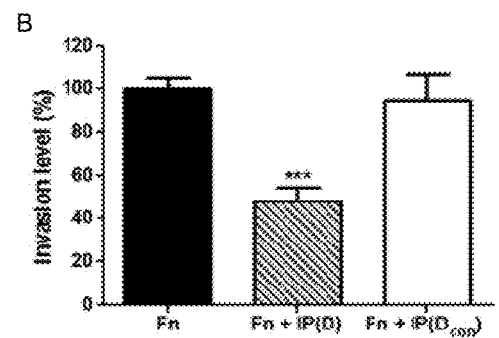

Inhibitory Peptide Made Up of D-Amino Acids Prevents Fn from Binding and Invading Host Cells As illustrated in FIG. 9, we found that we could use an inhibitory peptide made up of D-amino acids to prevent Fn from binding and invading host cells. This finding significantly substantiates the potential usage of the inhibitory peptide because all natural peptides are made of L-amino acids, which get degraded by the peptidases easily. The D-amino acids, on the other hand, are not naturally occurring, thus are resistant to degradation.

Detection of Subspecies of Fn in Saliva

Figure 10:
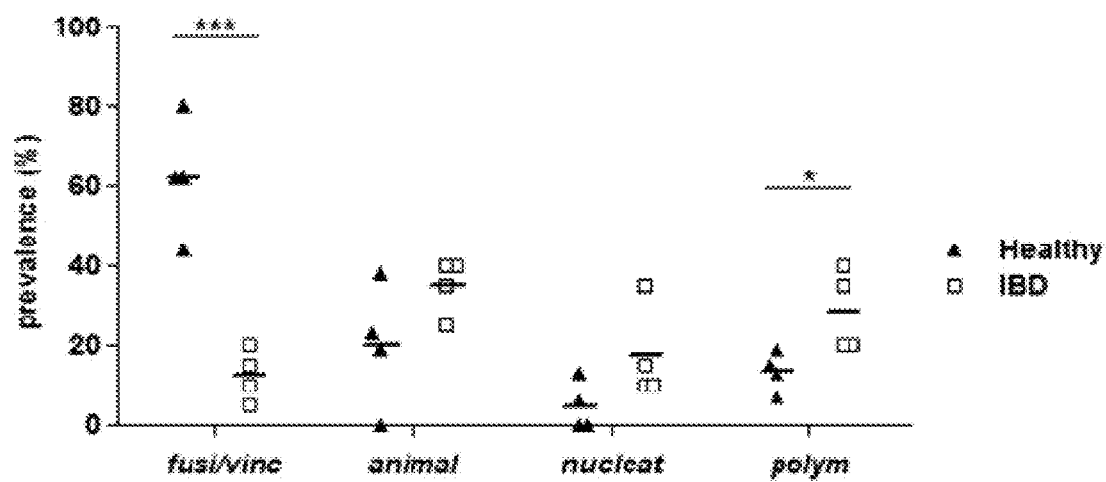
FIG. 10 illustrates the prevalence of Fn subsp in saliva of healthy individuals and patients with IBD. Each symbol represents one individual. Short bars represent the mean value. *** $p<0.001$; * $p<0.05$.

We have found that the five subspecies (subsp) of Fn, i.e., subsp *animalis*, subsp *fusiforme*, subsp *nucleatum*, subsp *polymorphum*, and subsp *vincentii*, are distributed differently in the saliva of normal people and patients with inflammatory bowel disease (IBD). As shown in FIG. 10 below, normal individuals harbor higher levels of subsp *fusiforme* and subsp *vincentii*. These two subsp are indistinguishable based on 16S rRNA gene sequences, thus we collectively group them as "subsp *fusiforme/vincentii*". We have designed primers which can specifically detect subsp *fusiforme/vincentii*, which we believe have tremendous diagnostic potential. We propose to quantify salivary subsp *fusiforme/vincentii* levels for identification of patients with GI disorders including but not limited to gastritis, IBD, and cancer.

The new primers developed include: For specific detection of subsp *animalis* by qPCR: 5'GCTAGGGA-CAACATTTAGAAAT (SEQ ID NO: 46) and 5'ACG-CAAAGCTCTCTCACAGT (SEQ ID NO: 47).

For specific detection of subsp *fusiforme/vincentii* by qPCR: 5'CTTGAATTTGGGTTTTTAACTTAGG (SEQ ID NO: 48) (and 5'CACAGCGCTTATAGCTTTCATAATTA (SEQ ID NO: 49).

For specific amplification of all Fusobacteria by end-point PCR: GGATTAGATACCCTGGTAGTC (SEQ ID NO: 50) and CTCTTTCGTATTAAGACTCCA (SEQ ID NO: 51), or 5'GGATTAGATACCCTGGTAGTC (SEQ ID NO: 52) and 5'CCAATAGAATAGAGAAAGACT (SEQ ID NO: 53).

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of identifying a subject with increased risk of colorectal cancer, the method comprising:
   obtaining a biological sample from the subject;
   measuring the level of FadA expression in the biological sample, wherein FadA expression is measured by measuring FadA mRNA levels using PCR wherein a first primer having SEQ ID NO: 44 and second primer having SEQ ID NO: 45 is used in the PCR to amplify the mRNA in the sample; and
   determining whether the subject has an increased risk of colorectal cancer by comparing the measured FadA expression to a control level, wherein an increased measured FadA expression compared to the control level is indicative of increased risk of colorectal cancer in the subject.

2. The method of claim 1, wherein the biological sample comprises at least one of colon biopsies, saliva, rectal swabs, or a bodily fluid.

3. The method of claim 2, wherein the bodily fluid comprises at least one of blood, amniotic fluid, lung aspirate, saliva, or synovial fluid.

4. The method of claim 1, further comprising measuring *Fusobacterium nucleatum* (Fn) 16S rRNA levels and normalizing the measured FadA mRNA levels to the Fn 16s rRNA levels, wherein an increased normalized FadA mRNA level is indicative of the subject having colorectal cancer.

5. A method of differentiating precancerous and cancerous states in a subject at risk of or suspected of having colorectal cancer, the method comprising:
   obtaining a biological sample from the subject;
   measuring the level of FadA expression in the biological sample, wherein FadA expression is measured by measuring FadA mRNA levels using PCR wherein a first primer having SEQ ID NO: 44 and second primer having SEQ ID NO: 45 is used in the PCR to amplify the mRNA in the sample;

measuring the 16S rRNA levels of *Fusobacterium nucleatum* in the sample;

normalizing FadA mRNA levels to 16S rRNA levels of *Fusobacterium nucleatum*; and differentiating precancerous and cancerous states in the subject by comparing the measured FadA mRNA levels to control levels and to 16S rRNA levels of *Fusobacterium nucleatum*, wherein increased measured FadA mRNA levels compared to control levels is indicative of the biological sample being in precancerous or cancerous state and increased measured FadA mRNA levels compared to 16S rRNA levels of *Fusobacterium nucleatum* is indicative of the biological sample being in a cancerous state.

6. The method of claim 5, wherein the biological sample comprises at least one of colon biopsies, saliva, rectal swabs, or a bodily fluid.

7. The method of claim 6, wherein the bodily fluid comprises at least one of blood, amniotic fluid, lung aspirate, saliva, or synovial fluid.

8. The method of claim 5, wherein the *Fusobacterium nucleatum* (Fn) 16S rRNA levels is measured using PCR.

9. The method of claim 8, wherein the rRNA is amplified by at least one primer pair having the nucleic sequences of SEQ ID NO: 42 and SEQ ID NO: 43, SEQ ID NO: 46 and SEQ ID NO: 47, SEQ ID NO: 48 and SEQ ID NO: 49, SEQ ID NO: 50 and SEQ ID NO: 51, or SEQ ID NO: 52 and SEQ ID NO: 53.

* * * * *

SEQUENCE LISTING

```
<160> NUMBER OF SEQ ID NOS: 64

<210> SEQ ID NO 1
<211> LENGTH: 10
<212> TYPE: PRT
<213> ORGANISM: Artificial Sequence
<220> FEATURE:
<223> OTHER INFORMATION: Synthetic Amino Acid

<400> SEQUENCE: 1

Ala Ser Ala Asn Trp Thr Ile Gln Tyr Asn
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Amino Acid

<400> SEQUENCE: 2

Asn Asn Phe Thr Leu Thr Asp Asn His Asp Asn
1               5                   10
```

<210> SEQ ID NO 3
<211> LENGTH: 30
<212> TYPE: DNA
<213> ORGANISM: Artificial Sequence
<220> FEATURE:
<223> OTHER INFORMATION: Synthetic Nucleotide

<400> SEQUENCE: 3
ggccgtcgac gactgggtta ttcctcccat                              30

<210> SEQ ID NO 4
<211> LENGTH: 30
<212> TYPE: DNA
<213> ORGANISM: Artificial Sequence
<220> FEATURE:
<223> OTHER INFORMATION: Synthetic Nucleotide

<400> SEQUENCE: 4
ggccgaattc acccaggagg tctttaaggg                              30

<210> SEQ ID NO 5
<211> LENGTH: 35
<212> TYPE: DNA
<213> ORGANISM: Artificial Sequence
<220> FEATURE:
<223> OTHER INFORMATION: Synthetic Nucleotide

<400> SEQUENCE: 5
ggccgcggcc gcttagaaga tcggaggatt atcgt                        35

<210> SEQ ID NO 6
<211> LENGTH: 30
<212> TYPE: DNA
<213> ORGANISM: Artificial Sequence
<220> FEATURE:
<223> OTHER INFORMATION: Synthetic Nucleotide

<400> SEQUENCE: 6
ggccgaattc aatcccacca cgtacaaggg                              30

<210> SEQ ID NO 7
<211> LENGTH: 35
<212> TYPE: DNA
<213> ORGANISM: Artificial Sequence
<220> FEATURE:
<223> OTHER INFORMATION: Synthetic Nucleotide

<400> SEQUENCE: 7
ggccgcggcc gcttaaaaga tgggggcttc attca                        35

<210> SEQ ID NO 8
<211> LENGTH: 30
<212> TYPE: DNA
<213> ORGANISM: Artificial Sequence
<220> FEATURE:
<223> OTHER INFORMATION: Synthetic Nucleotide

<400> SEQUENCE: 8
ggccgaattc gtgcctcctg aaaagagagt                              30

<210> SEQ ID NO 9
<211> LENGTH: 33
<212> TYPE: DNA
<213> ORGANISM: Artificial Sequence
<220> FEATURE:

<223> OTHER INFORMATION: Synthetic Nucleotide

<400> SEQUENCE: 9
ggccctcgag ttaggggggcg ttgtcattca cat    33

<210> SEQ ID NO 10
<211> LENGTH: 30
<212> TYPE: DNA
<213> ORGANISM: Artificial Sequence
<220> FEATURE:
<223> OTHER INFORMATION: Synthetic Nucleotide

<400> SEQUENCE: 10
ggccgaattc ataccagaac ctcgaactat    30

<210> SEQ ID NO 11
<211> LENGTH: 33
<212> TYPE: DNA
<213> ORGANISM: Artificial Sequence
<220> FEATURE:
<223> OTHER INFORMATION: Synthetic Nucleotide

<400> SEQUENCE: 11
ggccctcgag ttacttccta cagacgccag cgg    33

<210> SEQ ID NO 12
<211> LENGTH: 30
<212> TYPE: DNA
<213> ORGANISM: Artificial Sequence
<220> FEATURE:
<223> OTHER INFORMATION: Synthetic Nucleotide

<400> SEQUENCE: 12
ggccgaattc cttgctttgc taattctgat    30

<210> SEQ ID NO 13
<211> LENGTH: 33
<212> TYPE: DNA
<213> ORGANISM: Artificial Sequence
<220> FEATURE:
<223> OTHER INFORMATION: Synthetic Nucleotide

<400> SEQUENCE: 13
ggccctcgag ttagtcgtcc tcgccgcctc cgt    33

<210> SEQ ID NO 14
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 14
atcattgatg cagaccttcc    20

<210> SEQ ID NO 15
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 15
gaattccggg gatcccaggg    20

```
<210> SEQ ID NO 16
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 16
acacacgggg cgagtgccaa                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 17
gtttatgacc tgaggctttg                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 18
acacacgggg cgagtgccaa                                                   20

<210> SEQ ID NO 19
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 19
tagttctgct gtgaagggag                                                   20

<210> SEQ ID NO 20
<211> LENGTH: 21
<212> TYPE: DNA
<213> ORGANISM: Artificial Sequence
<220> FEATURE:
<223> OTHER INFORMATION: Synthetic Nucleotide

<400> SEQUENCE: 20
gacgccatca tcgtcatagg a                                                 21

<210> SEQ ID NO 21
<211> LENGTH: 18
<212> TYPE: DNA
<213> ORGANISM: Artificial Sequence
<220> FEATURE:
<223> OTHER INFORMATION: Synthetic Nucleotide

<400> SEQUENCE: 21
ggccattgcg gaactgaa                                                     18

<210> SEQ ID NO 22
<211> LENGTH: 20
<212> TYPE: DNA
<213> ORGANISM: Artificial Sequence
<220> FEATURE:
<223> OTHER INFORMATION: Synthetic Nucleotide
```

```
<400> SEQUENCE: 22
tgaagctcgg agcactgtca                                          20

<210> SEQ ID NO 23
<211> LENGTH: 19
<212> TYPE: DNA
<213> ORGANISM: Artificial Sequence
<220> FEATURE:
<223> OTHER INFORMATION: Synthetic Nucleotide

<400> SEQUENCE: 23
ggccaggaat cttgttgca                                           19

<210> SEQ ID NO 24
<211> LENGTH: 18
<212> TYPE: DNA
<213> ORGANISM: Artificial Sequence
<220> FEATURE:
<223> OTHER INFORMATION: Synthetic Nucleotide

<400> SEQUENCE: 24
gggcagacgg tcaagcaa                                            18

<210> SEQ ID NO 25
<211> LENGTH: 21
<212> TYPE: DNA
<213> ORGANISM: Artificial Sequence
<220> FEATURE:
<223> OTHER INFORMATION: Synthetic Nucleotide

<400> SEQUENCE: 25
ccagccttga tcaccttcac a                                        21

<210> SEQ ID NO 26
<211> LENGTH: 22
<212> TYPE: DNA
<213> ORGANISM: Artificial Sequence
<220> FEATURE:
<223> OTHER INFORMATION: Synthetic Nucleotide

<400> SEQUENCE: 26
ctgggtgctc ctgttcttcc ta                                       22

<210> SEQ ID NO 27
<211> LENGTH: 19
<212> TYPE: DNA
<213> ORGANISM: Artificial Sequence
<220> FEATURE:
<223> OTHER INFORMATION: Synthetic Nucleotide

<400> SEQUENCE: 27
gaggcggagg tccagaatg                                           19

<210> SEQ ID NO 28
<211> LENGTH: 18
<212> TYPE: DNA
<213> ORGANISM: Artificial Sequence
<220> FEATURE:
<223> OTHER INFORMATION: Synthetic Nucleotide

<400> SEQUENCE: 28
cctcgcgggt ctcctgtt                                            18

<210> SEQ ID NO 29
<211> LENGTH: 22
```

```
<212> TYPE: DNA
<213> ORGANISM: Artificial Sequence
<220> FEATURE:
<223> OTHER INFORMATION: Synthetic Nucleotide

<400> SEQUENCE: 29
aggcccagaa tctcattgct ta                                              22

<210> SEQ ID NO 30
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 30
cctagtgctg catgaggaga                                                 20

<210> SEQ ID NO 31
<211> LENGTH: 23
<212> TYPE: DNA
<213> ORGANISM: Artificial Sequence
<220> FEATURE:
<223> OTHER INFORMATION: Synthetic Nucleotide

<400> SEQUENCE: 31
tcttcctcat cttcttgctc ttc                                             23

<210> SEQ ID NO 32
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 32
tgccctctgt gccacagatg                                                 20

<210> SEQ ID NO 33
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 33
tctggagagg aagcgtgtga                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 34
aacggtcctg ctgatggcta                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 35
```

```
atccagctct tgcagccgtt                                              20

<210> SEQ ID NO 36
<211> LENGTH: 18
<212> TYPE: DNA
<213> ORGANISM: Artificial Sequence
<220> FEATURE:
<223> OTHER INFORMATION: Synthetic Nucleotide

<400> SEQUENCE: 36
cggaaccgtg gttctttg                                                18

<210> SEQ ID NO 37
<211> LENGTH: 18
<212> TYPE: DNA
<213> ORGANISM: Artificial Sequence
<220> FEATURE:
<223> OTHER INFORMATION: Synthetic Nucleotide

<400> SEQUENCE: 37
actcggcttc tcgctgac                                                18

<210> SEQ ID NO 38
<211> LENGTH: 19
<212> TYPE: DNA
<213> ORGANISM: Artificial Sequence
<220> FEATURE:
<223> OTHER INFORMATION: Synthetic Nucleotide

<400> SEQUENCE: 38
tgcaccacca actgcttag                                               19

<210> SEQ ID NO 39
<211> LENGTH: 18
<212> TYPE: DNA
<213> ORGANISM: Artificial Sequence
<220> FEATURE:
<223> OTHER INFORMATION: Synthetic Nucleotide

<400> SEQUENCE: 39
gatgcaggga tgatgttc                                                18

<210> SEQ ID NO 40
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 40
actcctacgg gaggcagcag                                              20

<210> SEQ ID NO 41
<211> LENGTH: 17
<212> TYPE: DNA
<213> ORGANISM: Artificial Sequence
<220> FEATURE:
<223> OTHER INFORMATION: Synthetic Nucleotide

<400> SEQUENCE: 41
attaccgcgg ctgctgg                                                 17

<210> SEQ ID NO 42
<211> LENGTH: 21
<212> TYPE: DNA
<213> ORGANISM: Artificial Sequence
```

```
<220> FEATURE:
<223> OTHER INFORMATION: Synthetic Nucleotide

<400> SEQUENCE: 42
cttaggaatg agacagagat g                                              21

<210> SEQ ID NO 43
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 43
tgatggtaac atacgaaagg                                                20

<210> SEQ ID NO 44
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 44
gaagaaagag cacaagctga                                                20

<210> SEQ ID NO 45
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 45
gcttgaagtc tttgagctct                                                20

<210> SEQ ID NO 46
<211> LENGTH: 22
<212> TYPE: DNA
<213> ORGANISM: Artificial Sequence
<220> FEATURE:
<223> OTHER INFORMATION: Synthetic Nucleotide

<400> SEQUENCE: 46
gctagggaca acatttagaa at                                             22

<210> SEQ ID NO 47
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 47
acgcaaagct ctctcacagt                                                20

<210> SEQ ID NO 48
<211> LENGTH: 25
<212> TYPE: DNA
<213> ORGANISM: Artificial Sequence
<220> FEATURE:
<223> OTHER INFORMATION: Synthetic Nucleotide

<400> SEQUENCE: 48
cttgaatttg ggttttaac ttagg                                           25
```

<210> SEQ ID NO 49
<211> LENGTH: 26
<212> TYPE: DNA
<213> ORGANISM: Artificial Sequence
<220> FEATURE:
<223> OTHER INFORMATION: Synthetic Nucleotide

<400> SEQUENCE: 49
cacagcgctt atagctttca taatta                                26

<210> SEQ ID NO 50
<211> LENGTH: 21
<212> TYPE: DNA
<213> ORGANISM: Artificial Sequence
<220> FEATURE:
<223> OTHER INFORMATION: Synthetic Nucleotide

<400> SEQUENCE: 50
ggattagata ccctggtagt c                                     21

<210> SEQ ID NO 51
<211> LENGTH: 21
<212> TYPE: DNA
<213> ORGANISM: Artificial Sequence
<220> FEATURE:
<223> OTHER INFORMATION: Synthetic Nucleotide

<400> SEQUENCE: 51
ctctttcgta ttaagactcc a                                     21

<210> SEQ ID NO 52
<211> LENGTH: 21
<212> TYPE: DNA
<213> ORGANISM: Artificial Sequence
<220> FEATURE:
<223> OTHER INFORMATION: Synthetic Nucleotide

<400> SEQUENCE: 52
ggattagata ccctggtagt c                                     21

<210> SEQ ID NO 53
<211> LENGTH: 21
<212> TYPE: DNA
<213> ORGANISM: Artificial Sequence
<220> FEATURE:
<223> OTHER INFORMATION: Synthetic Nucleotide

<400> SEQUENCE: 53
ccaatagaat agagaaagac t                                     21

<210> SEQ ID NO 54
<211> LENGTH: 72
<212> TYPE: PRT
<213> ORGANISM: Artificial Sequence
<220> FEATURE:
<223> OTHER INFORMATION: Synthetic Amino Acid

<400> SEQUENCE: 54

Ile Pro Glu Pro Arg Thr Ile Phe Phe Cys Glu Arg Asn Pro Lys Pro
1               5                   10                  15

Gln Val Ile Asn Ile Ile Asp Ala Asp Leu Pro Pro Asn Thr Ser Pro
            20                  25                  30

Phe Thr Ala Glu Leu Thr His Gly Ala Ser Ala Asn Trp Thr Ile Gln
        35                  40                  45

Tyr Asn Asp Pro Thr Gln Glu Ser Ile Ile Leu Lys Pro Lys Met Ala
    50                  55                  60

Leu Glu Val Gly Asp Tyr Lys Ile
 65              70

<210> SEQ ID NO 55
<211> LENGTH: 15
<212> TYPE: PRT
<213> ORGANISM: Artificial Sequence
<220> FEATURE:
<223> OTHER INFORMATION: Synthetic Amino Acid

<400> SEQUENCE: 55

Thr His Gly Ala Ser Ala Asn Trp Thr Ile Gln Tyr Asn Asp Pro
 1               5                  10                  15

<210> SEQ ID NO 56
<211> LENGTH: 14
<212> TYPE: PRT
<213> ORGANISM: Artificial Sequence
<220> FEATURE:
<223> OTHER INFORMATION: Synthetic Amino Acid

<400> SEQUENCE: 56

His Gly Ala Ser Ala Asn Trp Thr Ile Gln Tyr Asn Asp Pro
 1               5                  10

<210> SEQ ID NO 57
<211> LENGTH: 13
<212> TYPE: PRT
<213> ORGANISM: Artificial Sequence
<220> FEATURE:
<223> OTHER INFORMATION: Synthetic Amino Acid

<400> SEQUENCE: 57

Gly Ala Ser Ala Asn Trp Thr Ile Gln Tyr Asn Asp Pro
 1               5                  10

<210> SEQ ID NO 58
<211> LENGTH: 12
<212> TYPE: PRT
<213> ORGANISM: Artificial Sequence
<220> FEATURE:
<223> OTHER INFORMATION: Synthetic Amino Acid

<400> SEQUENCE: 58

Ala Ser Ala Asn Trp Thr Ile Gln Tyr Asn Asp Pro
 1               5                  10

<210> SEQ ID NO 59
<211> LENGTH: 11
<212> TYPE: PRT
<213> ORGANISM: Artificial Sequence
<220> FEATURE:
<223> OTHER INFORMATION: Synthetic Amino Acid

<400> SEQUENCE: 59

Ser Ala Asn Trp Thr Ile Gln Tyr Asn Asp Pro
 1               5                  10

<210> SEQ ID NO 60
<211> LENGTH: 14
<212> TYPE: PRT
<213> ORGANISM: Artificial Sequence
<220> FEATURE:
<223> OTHER INFORMATION: Synthetic Amino Acid

```
<400> SEQUENCE: 60

Thr His Gly Ala Ser Ala Asn Trp Thr Ile Gln Tyr Asn Asp
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic Amino Acid

<400> SEQUENCE: 61

Thr His Gly Ala Ser Ala Asn Trp Thr Ile Gln Tyr Asn
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic Amino Acid

<400> SEQUENCE: 62

Thr His Gly Ala Ser Ala Asn Trp Thr Ile Gln Tyr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic Amino Acid

<400> SEQUENCE: 63

Thr His Gly Ala Ser Ala Asn Trp Thr Ile Gln
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic Amino Acid

<400> SEQUENCE: 64

Ala Ser Ala Asn Trp Thr Ile Gln Tyr Asn Asp
1               5                   10
```